United States Patent
Masumoto

(10) Patent No.: US 9,295,442 B2
(45) Date of Patent: Mar. 29, 2016

(54) MEDICAL IMAGE CONVERSION APPARATUS, METHOD AND PROGRAM

(75) Inventor: Jun Masumoto, Tokyo (JP)

(73) Assignee: FUJIFILM Corporation ko, Tokyo (JP)

(*) Notice: Subject to any disclaimer, the term of this patent is extended or adjusted under 35 U.S.C. 154(b) by 230 days.

(21) Appl. No.: 13/635,605

(22) PCT Filed: Mar. 17, 2011

(86) PCT No.: PCT/JP2011/001568
§ 371 (c)(1),
(2), (4) Date: Sep. 17, 2012

(87) PCT Pub. No.: WO2011/114733
PCT Pub. Date: Sep. 22, 2011

(65) Prior Publication Data
US 2013/0004039 A1    Jan. 3, 2013

(30) Foreign Application Priority Data

Mar. 17, 2010 (JP) .................... 2010-060398
Mar. 19, 2010 (JP) .................... 2010-063411

(51) Int. Cl.
*A61B 6/00* (2006.01)
*G06T 3/00* (2006.01)
*G06T 5/00* (2006.01)

(52) U.S. Cl.
CPC ............ *A61B 6/504* (2013.01); *A61B 6/481* (2013.01); *A61B 6/482* (2013.01); *A61B 6/5217* (2013.01); *G06T 3/0068* (2013.01); *G06T 5/008* (2013.01); *A61B 6/503* (2013.01); *G06T 2207/10076* (2013.01); *G06T 2207/30048* (2013.01); *G06T 2207/30061* (2013.01)

(58) Field of Classification Search
None
See application file for complete search history.

(56) References Cited

U.S. PATENT DOCUMENTS

| 5,910,972 | A | 6/1999 | Ohkubo et al. | |
|---|---|---|---|---|
| 6,289,135 | B1 * | 9/2001 | Declerck | G06T 7/2006 324/309 |
| 8,497,862 | B2 * | 7/2013 | Masumoto et al. | 345/424 |
| 8,638,328 | B2 * | 1/2014 | Lin | 345/419 |
| 2003/0233039 | A1 | 12/2003 | Shao et al. | |

(Continued)

FOREIGN PATENT DOCUMENTS

| JP | 10-108073 | 4/1998 |
|---|---|---|
| JP | 2005-528974 | 9/2005 |

(Continued)

OTHER PUBLICATIONS

Zhang et al. "A software Platform for Real-Time Visualizatino and Manipulation of 4D cardiac images" FIMH 2009, LNCS 5528, pp. 396-406, 2009, Springer-Verlag Berlin Heidelberg 2009.*
International Search Report, PCT/JP2011/001568, Apr. 26, 2011.
W.M. Wells III et al., "Multi-modal volume registration by maximization of mutual information", Medical Image Analysis, vol. 1, No. 1, pp. 35-51, 1996.

(Continued)

*Primary Examiner* — Bhavesh Mehta
*Assistant Examiner* — Oneal R Mistry
(74) *Attorney, Agent, or Firm* — Young & Thompson

(57) ABSTRACT

An image obtainment unit obtains a series of time series medical images about a specific organ in different phases. A registration unit performs registration of voxel positions in the series of time series medical images between the series of time series medical images. A conversion unit converts signal values at corresponding voxel positions of the specific organ into a same display voxel value in the series of time series medical images.

25 Claims, 12 Drawing Sheets

(56) References Cited

U.S. PATENT DOCUMENTS

| | | | |
|---|---|---|---|
| 2005/0249393 A1 | 11/2005 | Kropfeld | |
| 2007/0179377 A1 | 8/2007 | Carlsen et al. | |
| 2008/0144764 A1 | 6/2008 | Nishide et al. | |
| 2008/0270095 A1* | 10/2008 | Lombaert et al. | 703/11 |
| 2008/0287784 A1 | 11/2008 | Ohta et al. | |
| 2009/0245606 A1* | 10/2009 | Prince et al. | 382/130 |
| 2010/0254584 A1* | 10/2010 | Gulsun et al. | 382/131 |
| 2013/0034203 A1* | 2/2013 | Wang | A61B 6/03 378/41 |

FOREIGN PATENT DOCUMENTS

| | | |
|---|---|---|
| JP | 2005-322252 | 11/2005 |
| JP | 2007-159643 | 6/2007 |
| JP | 2007-516744 | 6/2007 |
| JP | 2008-148886 | 7/2008 |
| JP | 2008-173236 | 7/2008 |
| JP | 2008-284197 | 11/2008 |
| JP | 2009-178493 | 8/2009 |

OTHER PUBLICATIONS

J. Masumoto et al., "A similarity measure for nonrigid volume registration using known joint distribution of targeted tissue: Application to dynamic CT data of the liver", Medical Image Analysis, vol. 7, No. 4, pp. 553-564, 2003.

Y. Wang and L.H. Staib, "Physical model-based non-rigid registration incorporating statistical shape information", Medical Image Analysis, vol. 4, No. 1, pp. 7-21, 2000.

D. Rueckert et al., "Nonrigid Registration Using Free-Form Deformations: Application to Breast MR Images", IEEE Transactions on Medical Imaging, vol. 18, No. 8, pp. 712-721, Aug. 1999.

JP Office Action dated Jan. 31, 2012, with English Translation; Application No. 2010-060398.

JP Office Action dated Jan. 31, 2012, with English Translation; Application No. 2010-063411.

JP Office Action dated May 8, 2012, with English Translation; Application No. 2010-063411.

Chinese Official Action—201180014344.2—Apr. 25, 2014.

* cited by examiner

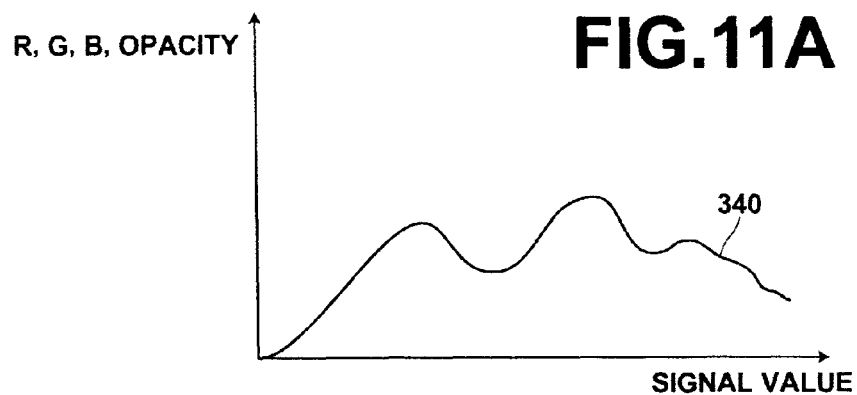
FIG.11A
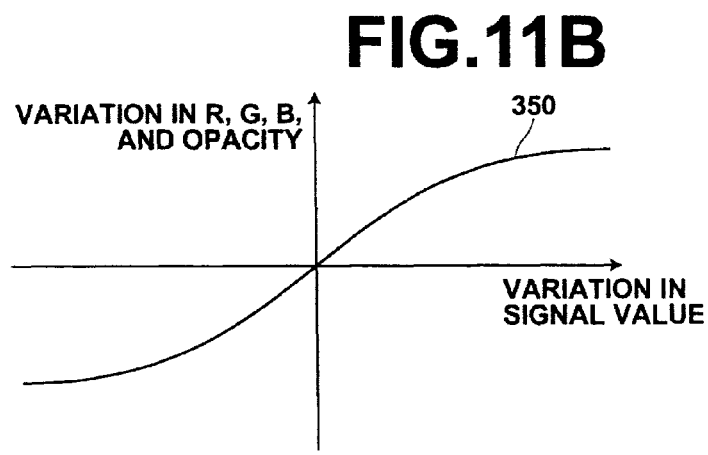
FIG.11B
FIG.12
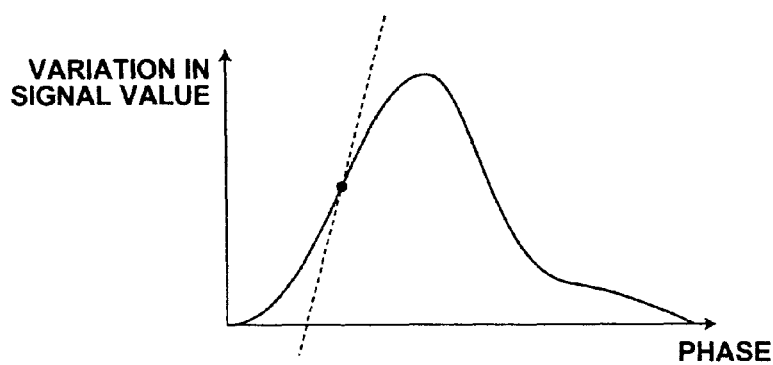

MEDICAL IMAGE CONVERSION APPARATUS, METHOD AND PROGRAM

BACKGROUND OF THE INVENTION

1. Field of the Invention

The present invention relates to a medical image conversion apparatus and method for converting time series medical images for representing the motion of an organ such as a heart, for example, to display them by volume rendering. Further, the present invention relates to a program for causing a computer to execute the medical image conversion method.

Further, the present invention relates to a medical image conversion apparatus and method for converting a series of plural medical images that have been obtained, for example, by imaging using a contrast agent, and the signal values of which change as time passes, to display the images by volume rendering, or the like. Further, the present invention relates to a program for causing a computer to execute the medical image conversion method.

2. Description of the Related Art

In recent years, high-quality three-dimensional images became used in image-based diagnosis because of an advance of medical equipment (for example, a multi-detector CT, or the like). Here, the three-dimensional image is composed of many two-dimensional tomographic images, and the information amount of the three-dimensional image is large. Therefore, in some cases, doctors need a time to find a desired observation region and to perform diagnosis on the region. Therefore, various techniques have been proposed to improve a characteristic of visually recognizing a whole structure, and also a lesion included in the structure. The visual recognition characteristic is improved by identifying a structure of interest, and by performing MIP display or the like of the structure of interest by generating a three-dimensional image of the structure of interest from a three-dimensional image including the structure of interest, for example, by using a maximum intensity projection method (MIP method), a minimum intensity projection method (MinIP method), or the like. Alternatively, volume rendering (VR) display of the three-dimensional image is performed, or CPR (Curved Planer Reconstruction) display is performed.

Meanwhile, the aforementioned multi-detector CT can obtain many tomographic images in one operation by plural detectors. Currently, more than 300 slices of tomographic images are obtainable in one rotation. Further, since one rotation of detectors needs about 0.3 second, if images of only a specific organ are obtained, plural three-dimensional images are obtainable in time series with short time intervals. An organ of interest included in the three-dimensional images that have been obtained in time series as described above is displayed in time series. In other words, four-dimensional display, which includes time in addition to the three-dimensional display, is performed. Accordingly, the state of the organ of interest in motion is observable as if a motion image is observed (please refer to Japanese Unexamined Patent Publication No. 2005-322252).

When the three-dimensional images are displayed four-dimensionally, as described above, especially, an analysis of a heart or the like in the field of circulatory organs becomes possible. Further, not only when images of an organ such as a heart or a lung, which has motion, are obtained, but also when three-dimensional images are obtained by using a contrast agent, the flow of the contrast agent is four-dimensionally displayed. Therefore, it is possible to diagnose a specific organ, such as a liver, by the effect of the contrast agent.

When a three-dimensional image is displayed by VR, an organ of interest is extracted. The extracted organ is three-dimensionally displayed by setting a color (R, G, B) and an opacity level (opacity) for the signal value of each voxel based on the signal value (a CT value if the image is a CT image) at each voxel position in the three-dimensional image of the extracted organ. When VR images are four-dimensionally displayed, the VR images are generated by setting colors and opacities for each of plural three-dimensional images, and the generated VR images are displayed in time series.

Meanwhile, when three-dimensional images are obtained by imaging a specific organ in time series with short time intervals, a signal value at a corresponding voxel position of the organ included in each of the three-dimensional images should be the same. However, in actual cases, a signal value at a corresponding voxel position of the same organ often differs from each other by an influence of noise during imaging, or the like. If a signal value at a corresponding voxel position of the same organ differs from each other, as described above, when VR images are four-dimensionally displayed, a color and an opacity at the same position of the organ fluctuate as the organ moves. If the color and the opacity of the organ fluctuate in such a manner, the three-dimensional motion of the position is falsely perceived, and there is a risk of failing to perform accurate diagnosis.

Further, when a series of three-dimensional images in different phases is obtained by imaging an organ such as a heart and a lung, which has motion, in time series with short time intervals, a signal value at a corresponding voxel position of the organ included in each of the three-dimensional images is the same value in many cases. However, when three-dimensional images are obtained in time series with short time intervals by using a contrast agent, the images are obtained to diagnose a temporal change in signal values. Therefore, a signal value at a voxel position of the same tissue included in each of the three-dimensional images differs from each other in many cases. Further, signal values of some tissue are the same in three-dimensional medical images of a certain phase, but different in three-dimensional medical images of another phase. As described above, if the signal value of the same tissue is different from each other in the three-dimensional medical images, depending on the phase, or if the signal values of different tissues are the same, it is impossible to distinguishably display different tissues when VR images are four-dimensionally displayed. If different tissues are not distinguishably displayed, as described above, there is a risk of failing to perform accurate diagnosis.

SUMMARY OF THE INVENTION

In view of the foregoing circumstances, it is an object of the present invention to prevent a fluctuation in colors or the like of medical images when the medical images are displayed in time series.

Further, in view of the foregoing circumstances, it is another object of the present invention to distinguishably display different tissues when a series of medical images are displayed, for example, in time series.

A first medical image conversion apparatus according to the present invention is a medical image conversion apparatus comprising:

an image obtainment means that obtains a series of time series medical images about a specific organ in different phases;

a registration means that performs registration of voxel positions in the series of time series medical images between the series of time series medical images; and a conversion means that converts signal values at corresponding voxel positions of the specific organ into a same display voxel value in the series of time series medical images.

As "a series of time series medical images in different phases", arbitrary images may be used as long as the images are obtained by successively imaging a specific organ of the same subject with short time intervals, and the motion of the specific organ can be regenerated by displaying the images in time series. Specifically, three-dimensional images, three-dimensional images of a specific organ extracted from three-dimensional images, two-dimensional images at a specific slice position including the specific organ in three-dimensional images, an image of a specific organ obtained by plain roentgenography, or the like may be used as the images.

The first medical image conversion apparatus of the present invention may further include a smoothing means that performs smoothing of the series of time series images before performing registration.

The first medical image conversion apparatus of the present invention may further include a display means that displays, in time series, the series of time series images after the conversion.

In the first medical image conversion apparatus of the present invention, the time series medical images may be three-dimensional medical images.

In the first medical image conversion apparatus of the present invention, the specific organ may be a heart and/or a lung.

A first medical image conversion method of the present invention is a medical image conversion method comprising the steps of:

obtaining a series of time series medical images about a specific organ in different phases;

performing registration of voxel positions in the series of time series medical images between the series of time series medical images; and converting signal values at corresponding voxel positions of the specific organ into a same display voxel value in the series of time series medical images.

The first medical image conversion method of the present invention may be provided as a program for causing a computer to execute the method.

According to the first medical image conversion apparatus and method, a series of time series medical images about a specific organ in different phases are obtained, and registration of voxel positions in the series of time series medical images is performed between the series of time series medical images, and signal values at corresponding voxel positions of the specific organ are converted into a same display voxel value in the series of time series medical images. Therefore, when a series of time series medical images are displayed in time series, a display voxel value of a part of a specific organ does not fluctuate even if the organ moves. Hence, the motion of a corresponding position in the specific organ is not falsely perceived. Consequently, it is possible to perform accurate diagnosis by using the medical images displayed in time series.

A second medical image conversion apparatus of the present invention is a medical image conversion apparatus comprising:

an image obtainment means that obtains a series of a plurality of medical images about a specific region; and a conversion means that converts, with respect to a target medical image to be converted of the series of medical images, a signal value at each voxel position in the target medical image into a display voxel value based on a variation between the signal value and a signal value at each corresponding voxel position in a base medical image that is used as a base.

As "a series of a plurality of medical images", plural medical images that have been obtained by successively imaging a specific region of the same subject with short time intervals, and which can display a change in signal values by displaying the medical images in time series, may be used. Further, plural medical images that have been obtained by imaging using plural kinds of radiation of different energies, and which can display a change in signal values in the medical images by displaying the medical images in the order of energy, may be used. The kind of medical images may be an arbitrary kind. Specifically, three-dimensional images, three-dimensional images of a specific organ extracted from three-dimensional images, two-dimensional images at a specific slice position including the specific organ in three-dimensional images, an image of a specific organ obtained by plain roentgenography, or the like may be used as the images.

The second medical image conversion apparatus of the present invention may further include a storage means that stores a color template defining a relationship among a first signal value that is used as a base, a second signal value that is obtained by changing the first signal value, and display voxel values for the first and second signal values. Further, the conversion means may convert, based on the base medical image, the signal value at each voxel position in the target medical image into the display voxel value with reference to the color template.

Further, the second medical image conversion apparatus of the present invention may further include a storage means that stores a color template defining a relationship between a first signal value that is used as a base and a display voxel value for the first signal value. Further, the conversion means may convert the signal value at each voxel position in the base medical image into the display voxel value with reference to the color template, and correct the display voxel value corresponding to each voxel position in the base medical image based on an index value representing a variation between the signal value at each voxel position in the target medical image and the signal value at the corresponding voxel position in the base medical image, and convert the signal value at each voxel position in the target medical image into the corrected display voxel value.

Further, the second medical image conversion apparatus of the present invention may further include a storage means that stores a color template representing a relationship between a first signal value that is used as a base and a display voxel value for the first signal value. Further, the conversion means may convert the signal value at each voxel position in the base medical image into the display voxel value with reference to the color template, and correct the display voxel value corresponding to each voxel position in the base medical image based on an index value representing a variation between the signal value at each voxel position in the target medical image and the signal value at the corresponding voxel position in the base medical image, and convert the signal value at each voxel position in the base medical image into the corrected display voxel value.

As "an index value representing a variation", a value that can represent a difference between a signal value at each voxel position in a target medical image and a signal value at a corresponding voxel position in a base medical image should be used. For example, besides the value of a difference from a signal value at a corresponding voxel position in the base medical image, the absolute value of the value of a difference, a logarithm value of the value of a difference, and the like may be used.

The second medical image conversion apparatus of the present invention may further include a display means that displays, in time series, the series of medical images after the conversion when the medical images have been obtained in time series.

Further, the second medical image conversion apparatus of the present invention may further include a display means that displays, in time series, the base medical image after the conversion in such a manner to be matched with the phase of the target medical image based on which the corrected display voxel value has been obtained when the medical images have been obtained in time series.

In the second medical image conversion apparatus of the present invention, the series of medical images may be obtained by performing radiography using a plurality of kinds of radiation of different energy from each other.

The second medical image conversion apparatus of the present invention may further includes a registration means that performs registration of voxel positions in the series of medical images between the series of medical images.

In this case, the second medical image conversion apparatus may further include a smoothing means that performs smoothing of the series of medical images before performing registration.

In the second medical image conversion apparatus of the present invention, the medical images may be three-dimensional medical images.

In the second medical image conversion apparatus of the present invention, the medical images may be obtained by imaging using a contrast agent.

A second medical image conversion method of the present invention is a medical image conversion method comprising the steps of:

obtaining a series of a plurality of medical images about a specific region; and converting, with respect to a target medical image to be converted of the series of medical images, a signal value at each voxel position in the target medical image into a display voxel value based on a variation between the signal value and a signal value at each corresponding voxel position in a base medical image that is used as a base.

The second medical image conversion method of the present invention may be provided as a program for causing a computer to execute the method.

According to the second medical image conversion apparatus and method of the present invention, a series of a plurality of medical images about a specific region are obtained. Further, with respect to a target medical image to be converted of the series of medical images, a signal value at each voxel position in the target medical image is converted into a display voxel value based on a variation between the signal value and a signal value at each corresponding voxel position in a base medical image that is used as a base. Therefore, even if the signal values of different tissues in a target medical image are the same, if the signal values change as time passes or the like, the tissues can be displayed at different display voxel values. Therefore, it is possible to distinguishably display different tissues at different display voxel values. Consequently, accurate diagnosis using a series of medical images displayed in a predetermined order is possible.

Further, with reference to a color template defining a relationship among a first signal value that is used as a base, a second signal value that is obtained by changing the first signal value, and display voxel values for the first and second signal values, the signal value at each voxel position in the target medical image is converted, based on the base medical image, into the display voxel value. Therefore, for example, even if signal values of tissues change in the same manner as time passes, if the signal values of the tissues differ from each other in the base medical image, it is possible to convert the signal values into different display voxel values by appropriately setting the color template. Further, even if the signal values of the same tissue differ from each other, the same tissue should originally have the same signal value. Therefore, if a medical image that has the same signal value for the same tissue is used as a base medical image, it is possible to display the same tissue at the same display voxel value.

Further, with reference to a color template defining a relationship between a first signal value that is used as a base and a display voxel value for the first signal value, a signal value at each voxel position in the base medical image is converted into a display voxel value. Further, the display voxel value corresponding to each voxel position in the base medical image is corrected based on an index value representing a variation between the signal value at each voxel position in the target medical image and the signal value at a corresponding voxel position in the base medical image, and the signal value at each voxel position in the target medical image is converted into the corrected display voxel value. Therefore, a change in signal values is certainly reflectable in a change in display voxel values. Hence, when a medical image in which signal values of the same tissue are the same and signal values of different tissues are different from each other is used as a base medical image, it is possible to certainly recognize a change in signal values in a series of medical images displayed in a predetermined order.

Further, with reference to a color template representing a relationship between a first signal value that is used as a base and a display voxel value for the first signal value, a signal value at each voxel position in the base medical image is converted into the display voxel value. Further, the display voxel value corresponding to each voxel position in the base medical image is corrected based on a variation between the signal value at each voxel position in the target medical image and the signal value at the corresponding voxel position in the base medical image, and the signal value at each voxel position in the base medical image is converted into the corrected display voxel value. Therefore, a change in signal values is certainly reflectable in a change in display voxel values. Hence, when a medical image in which signal values of the same tissue are the same and signal values of different tissues are different from each other is used as a base medical image, it is possible to certainly recognize a change in signal values in a series of base medical images displayed in a predetermined order in such a manner to be matched with the target medical image based on which the corrected display voxel value has been obtained.

BRIEF DESCRIPTION OF THE DRAWINGS

FIG. 11A is a diagram illustrating a color template for converting three-dimensional volume data in the fourth embodiment;

FIG. 11B is a diagram illustrating a color template for converting three-dimensional volume data in the fourth embodiment;

FIG. 12 is a diagram illustrating a point at which a variation in signal values is the highest;

DESCRIPTION OF THE PREFERRED EMBODIMENTS

Figure 1:
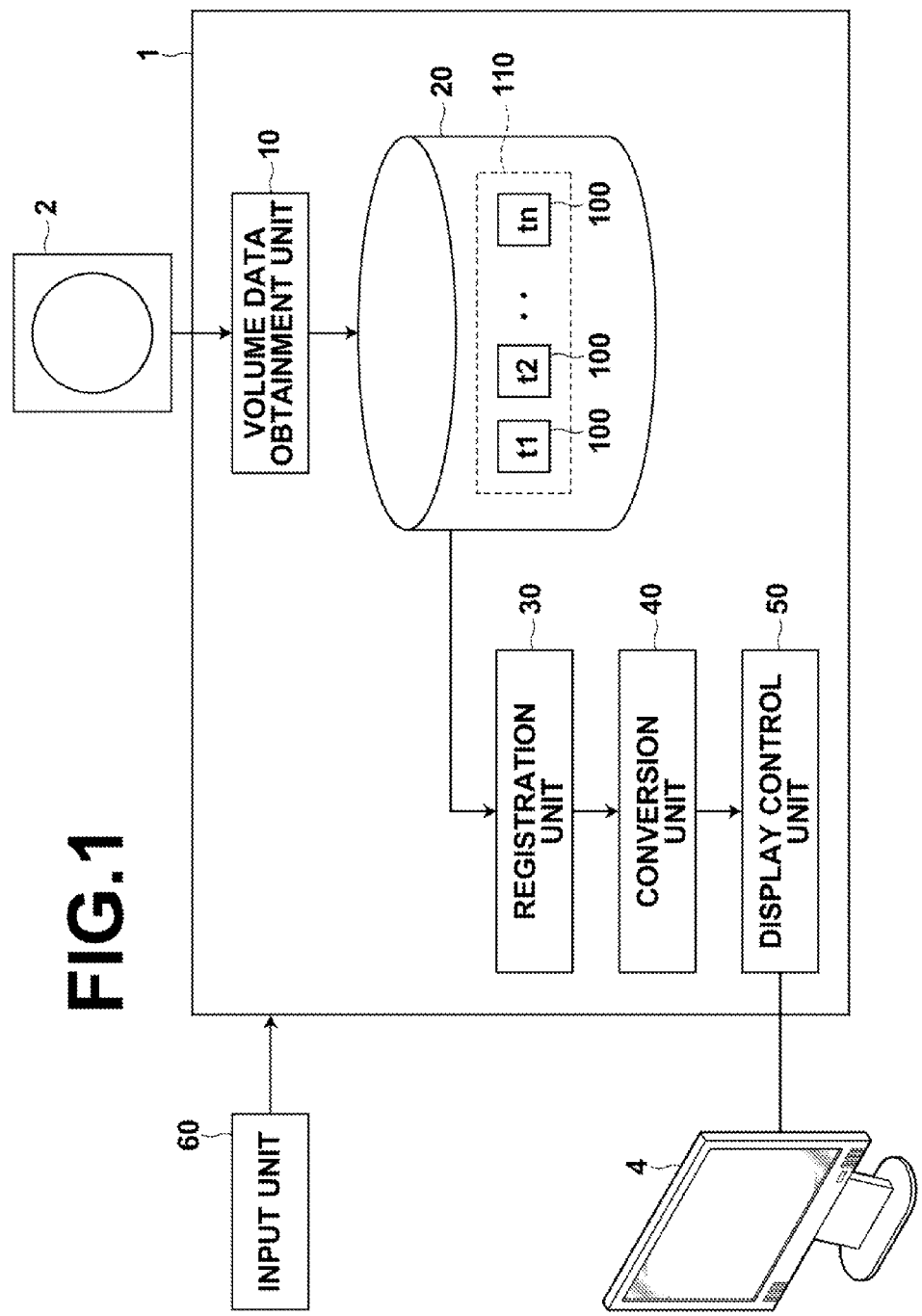
FIG. 1 is a schematic block diagram illustrating the configuration of a medical image conversion apparatus according to a first embodiment of the present invention.

Hereinafter, embodiments of the present invention will be described with reference to drawings. FIG. 1 is a schematic block diagram illustrating the configuration of a medical image conversion apparatus according to a first embodiment of the present invention. The configuration of a medical image conversion apparatus 1 illustrated in FIG. 1 is realized by causing a computer to execute a medical image conversion processing program that has been read in an auxiliary storage device. At this time, the medical image conversion processing program is stored in a storage medium, such as a CD-ROM, or distributed through a network, such as the Internet, and installed in the computer.

The medical image conversion apparatus 1 of the first embodiment includes a volume data obtainment unit 10, a storage unit 20, a registration unit 30, a conversion unit 40, a display control unit 50 and an input unit 60.

The volume data obtainment unit 10 has a communication interface function for obtaining a three-dimensional volume data group 110 composed of plural sets of three-dimensional volume data 100 obtained by imaging a specific organ of a subject with predetermined time intervals Δt at a modality 2, such as a CT apparatus and an MRI apparatus. The three-dimensional volume data group 110 is sent from the modality 2 through LAN. Further, in the first embodiment, the specific organ is assumed to be a heart.

Here, the three-dimensional volume data 100 are obtained by placing, one on another, sets of two-dimensional tomographic image data that have been sequentially obtained along a direction perpendicular to a cross section of a heart to be diagnosed. In the first embodiment, the three-dimensional volume data 100 are generated by placing, one on another, plural tomographic images obtained by imaging at the modality 2, such as a CT apparatus and an MRI apparatus. When volume data are obtained by using a CT apparatus, the volume data store an absorption amount of X-rays for each voxel (in other words, a voxel position). In the volume data, a signal value (if an image is obtained by imaging by a CT apparatus, a value representing an absorption amount of X-rays) has been provided for each voxel position.

The three-dimensional volume data group 110 is composed of a series of three-dimensional volume data 100 obtained, for example, by imaging a subject in different phases t1, t2, ... to with constant time intervals Δt.

Here, supplementary information defined by DICOM (Digital Imaging and Communications in Medicine) standard is attached to the three-dimensional volume data 100. The supplementary information may include, for example, an image ID for identifying a three-dimensional image represented by each set of three-dimensional volume data 100, a patient's ID for identifying a subject, an examination ID for identifying an examination, a unique ID (UID) allocated to each image information, an examination date and an examination time when the image information was generated, the kind of a modality used in an examination for obtaining the image information, patient's information, such as a patient's name, age and sex, an examined region (imaged region, and a heart in the first embodiment), an imaging condition (whether a contrast agent is used or not, a radiation dose, and the like), and when plural images were obtained in one examination, information such as a series number or a collection number.

The storage unit 20 is a large capacity storage device, such as a hard disk, and the three-dimensional volume data group 110 is stored in the storage unit 20. Here, plural three-dimensional volume data groups 110 of different subjects (in other words, different patients), or plural three-dimensional volume data groups 110 of the same subject at different imaging time are stored in the storage unit 20.

The registration unit 30 performs registration of corresponding voxel positions in a heart region between sets of three-dimensional volume data 100 for each set of three-dimensional volume data 100. Specifically, the registration unit 30 may correlate corresponding voxel positions to each other by using techniques disclosed in W. M. Wells III et al., "Multi-modal volume registration by maximization of mutual information", Medical Image Analysis, Vol. 1, No. 1, pp. 35-51, 1996 (Reference Document 1), D. Rueckert et al., "Nonrigid Registration Using Free-Form Deformations: Application to Breast MR Images", IEEE Transactions on Medical Imaging, Vol. 18, No. 8, pp. 712-721, 1999 (Reference Document 2), J. Masumoto et al., "A similarity measure for nonrigid volume registration using known joint distribution of targeted tissue: Application to dynamic CT data of the liver", Medical Image Analysis, Vol. 7, No. 4, pp. 553-564, 2003 (Reference Document 3), and Y. Wang and L. H. Staib, "Physical model-based non-rigid registration incorporating statistical shape information", Medical Image Analysis, Vol. 4, No. 1, pp. 7-20, 2000 (Reference Document 4).

The technique disclosed in Reference Document 1 performs registration using a rigid registration technique. In Reference Document 1, registration of the positions of voxels is performed by adjusting the positions and the directions of voxels between three-dimensional medical images obtained by different modalities in such a manner to maximize a mutual information amount. The technique disclosed in Reference Document 2 performs registration by using a non-rigid registration technique. In Reference Document 2, registration is performed on MRI images by using a deformation estimation method based on a B spline function, which is called as "free from deformation" (FFT). The technique disclosed in Reference Document 3 performs registration by using a non-rigid registration technique. In Reference Document 3, registration is performed by measuring a degree of similarity in CT images obtained in time series, and the degree of similarity is measured by sliding tissues at a boundary between a target tissue and a non-target tissue by using distribution of joint (joint distribution) of tissues of a liver or the like, as a target. The technique disclosed in Reference Document 4 performs registration between objects by using a non-rigid registration method. In Reference Document 4, the shape of an object is provided in advance, and registration is performed by transforming an object into the shape.

Alternatively, methods disclosed in PCT Japanese Publication No. 2005-528974 and PCT Japanese Publication No. 2007-516744 may be used. The technique disclosed in PCT Japanese Publication No. 2005-528974 obtains first and second image data sets from a region of interest of a target, and generates a physiological motion model, such as respiration and cardiac motion, with respect to the region of interest. Further, the physiological model is conformed to the first image data set, and a physiological phantom unique to the target is applied to the second image data set for transformation. Further, the transformation is applied to the first image data set to perform registration.

Further, the technique disclosed in PCT Japanese Publication No. 2007-516744 performs registration of images by performing registration of the positions of marks based on a similarity of the positions of the marks between two images.

The registration unit 30 performs registration between hearts included in three-dimensional images represented by the three-dimensional volume data 100 by using these techniques. Accordingly, voxels representing the same position of the heart included in the three-dimensional images are correlated to each other.

The registration method is not limited to the aforementioned methods. An arbitrary known technique is adoptable. Further, three-dimensional volume data 100 may be sequentially displayed on a monitor 4, and an operator may perform registration by an input from an input unit 60. Further, instead of performing registration of only the heart region, registration may be performed on all voxel positions of the three-dimensional volume data 100.

Figure 2A:
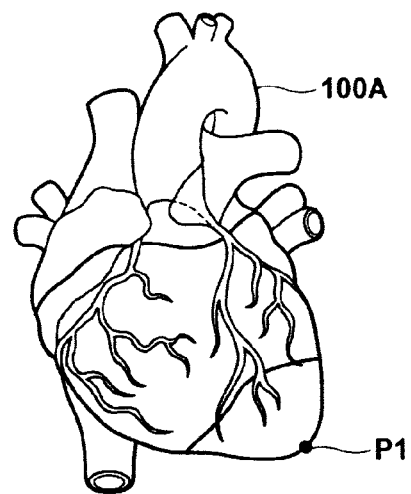
FIG. 2A is a diagram illustrating a result of registration in a three-dimensional image of a heart.
Figure 2B:
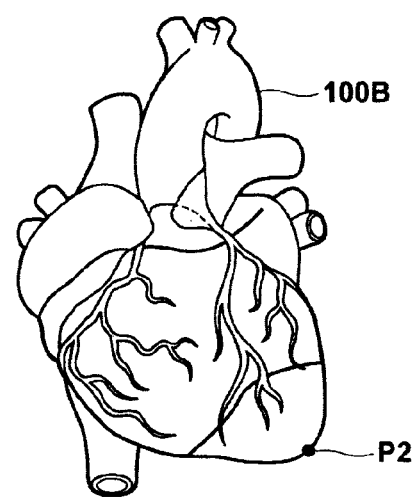
FIG. 2B is a diagram illustrating a result of registration in a three-dimensional image of a heart.
Figure 2C:
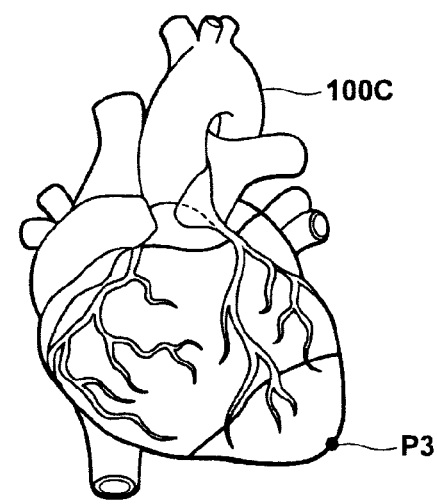
FIG. 2C is a diagram illustrating a result of registration in a three-dimensional image of a heart.

FIGS. 2A through 2C are diagrams illustrating a result of registration of three-dimensional images of a heart. FIGS. 2A through 2C illustrate a result of registration of the heart included in three sets of three-dimensional volume data 100A, 100B, 100C. As illustrated in FIGS. 2A through 2C, voxel P1 on the heart included in the three-dimensional volume data 100A is correlated to voxels P2, P3 of three-dimensional volume data 100B, 100C, respectively.

Figure 3:
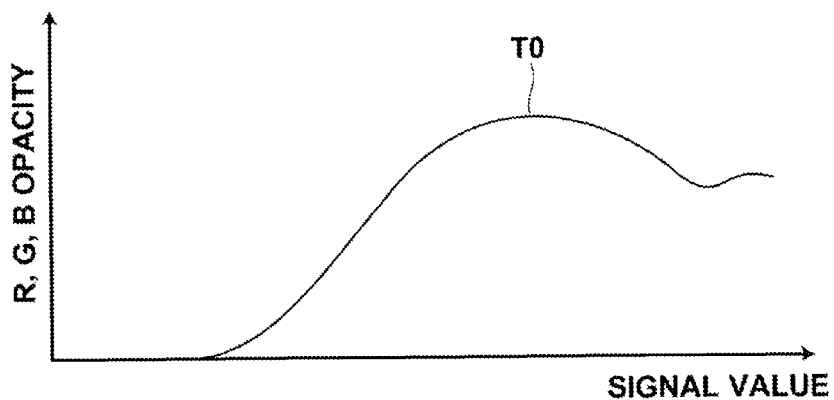
FIG. 3 is a diagram illustrating a color template.

The conversion unit 40 converts a signal value at each voxel position of the three-dimensional volume data into a display voxel value for performing volume rendering (VR) display. FIG. 3 is a diagram illustrating a color template for converting the three-dimensional volume data 100. Plural color templates are prepared in advance for regions to be extracted from the three-dimensional volume data 100 for VR display. In the first embodiment, it is assumed that color template T0 for displaying a heart by VR is selected. As illustrated in FIG. 3, the color template T0 is a one-dimensional lookup table, and signal values of the three-dimensional volume data 100 are set on the horizontal axis, and color (R, G, B) and opacity are set on the vertical axis. In FIG. 3, only one color template is illustrated. Actually, four color templates are provided for the colors of R, G and B and opacity, respectively.

The conversion unit 40 refers to the color template T0, and converts the signal value of each voxel of the three-dimensional volume data 100 into a display voxel value composed of R, G, B and opacity. At this time, the conversion unit 40 selects one base phase B, which is a base of phases of plural sets of three-dimensional volume data 100. Further, the conversion unit 40 converts a signal value at each voxel position of the three-dimensional volume data 100 in phases other than the base phase into a signal value at a corresponding voxel position in three-dimensional volume data in the base phase B (hereinafter, referred to as base three-dimensional volume data 120).

Here, selection of the base phase B should be performed by selecting a predetermined phase, for example, such as a first phase, or a middle phase, or a last phase of phases of the three-dimensional volume data group 110, and a phase when lowest-noise three-dimensional volume data 100 were obtained. Alternatively, selection of a phase, as base phase B, may be received by an input from the input unit 60. In this case, an operator should select, as the base phase B, a phase when lowest-noise three-dimensional volume data 100 were obtained, or the like.

Further, the conversion unit 40 converts a signal value at each voxel position in all the sets of three-dimensional volume data 100 into a signal value at a corresponding voxel position in base three-dimensional volume data 120. After then, the conversion unit 40 converts a signal value of each of sets of three-dimensional volume data 100 into a display voxel value by using a color template T0. Accordingly, the three-dimensional volume data 100 represent a VR image obtained by extracting a heart.

Consequently, corresponding voxel positions P1, P2, P3 in three sets of three-dimensional volume data 100A, 100B, 100C illustrated in FIGS. 2A through 2C are converted into a display voxel value of the same color and the same opacity even if the signal values at the voxel positions P1, P2, P3 are, for example, 100, 110, 107, respectively, by an influence of noise or the like. For example, when three-dimensional volume data in base phase B of the three sets of three-dimensional volume data 100A, 100B, 100C are three-dimensional volume data 100B, signal values at voxel positions P1, P3 are converted into 110. Consequently, the voxel positions P1, P3 are converted into a color and an opacity corresponding to the signal value of 110 in the color template 110.

The display control unit 50 displays, in time series, a VR image represented by a series of converted three-dimensional volume data 100 on the display 4. In the first embodiment, the VR image represents the heart. Therefore, the pulsation of the heart is displayed on the display 4.

The input unit 60 is composed of a known input device, such as a keyboard and a mouse.

Figure 4:
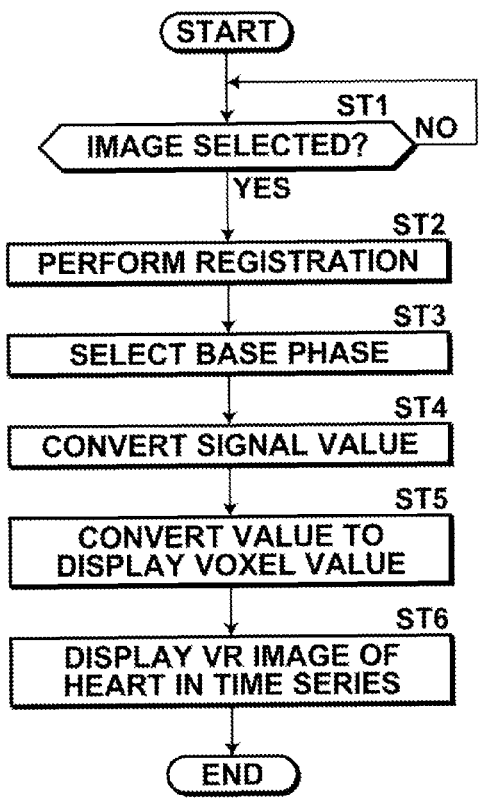
FIG. 4 is a flow chart illustrating processing in the first embodiment.

Next, processing performed in the first embodiment will be described. FIG. 4 is a flow chart illustrating processing performed in the first embodiment. Here, it is assumed that plural three-dimensional volume data groups 110 of a heart have been obtained by the volume data obtainment unit 10, and stored in the storage unit 20 in advance. When a three-dimensional image to be displayed is selected by operation of the input unit 60 by an operator (step ST1, YES), the registration unit 30 reads out a three-dimensional volume data group 110 corresponding to the selected three-dimensional image, and performs registration of voxel positions between sets of three-dimensional volume data 100 constituting the three-dimensional volume data group 110 (step ST2). Accordingly, voxel positions are correlated to each other between the sets of three-dimensional volume data 100.

Further, the conversion unit 40 selects base phase B (step ST3), and converts a signal value at each voxel position in all the sets of three-dimensional volume data 100 into a signal value at a corresponding voxel position in the base three-dimensional volume data 120 in the base phase B (step ST4). Further, the conversion unit 40 converts signal values of each set of three-dimensional volume data 100 into display voxel values by using the selected color template T0 (step ST5). Further, the display control unit 50 displays a VR image of a heart represented by the converted three-dimensional volume data 100 on the display 4 in time series (step ST6), and processing ends.

As described above, in the first embodiment, the registration unit 30 correlates voxel positions in sets of three-dimensional volume data 100 constituting the three-dimensional volume data group 110 to each other by performing registration of the voxel positions between the sets of three-dimensional volume data 100. Further, the conversion unit 40 selects base phase B, and converts a signal value at each voxel position in all the sets of three-dimensional volume data 100 into a signal value at a corresponding voxel position in the base three-dimensional volume data 120 in base phase B. Further, the conversion unit 40 converts a signal value of each set of three-dimensional volume data 100 into a display signal value composed of R, G, B and an opacity by using color template T0.

Therefore, when the three-dimensional volume data group 110 is displayed in time series, the color and the opacity at a voxel position in the heart does not fluctuate even if the heart moves. Hence, false perception of the three-dimensional motion of the heart that may be caused by a fluctuation of colors and opacities in the heart is prevented. Consequently, it is possible to perform accurate diagnosis by using the three-dimensional volume data group 110 displayed in time series.

In the above embodiment, the three-dimensional volume data group of a heart is used. Alternatively, a three-dimensional volume data group of a lung may be used. In this case, a VR image is four-dimensionally displayed in such a manner to represent the three-dimensional motion of the lung by respiration. Alternatively, a three-dimensional volume data group of circulatory organs including both of the heart and the lung may be used. In this case, the VR image is four-dimensionally displayed in such a manner to represent both of the three-dimensional motion of the heart by heartbeats and the three-dimensional motion of the lung by respiration.

Figure 5:
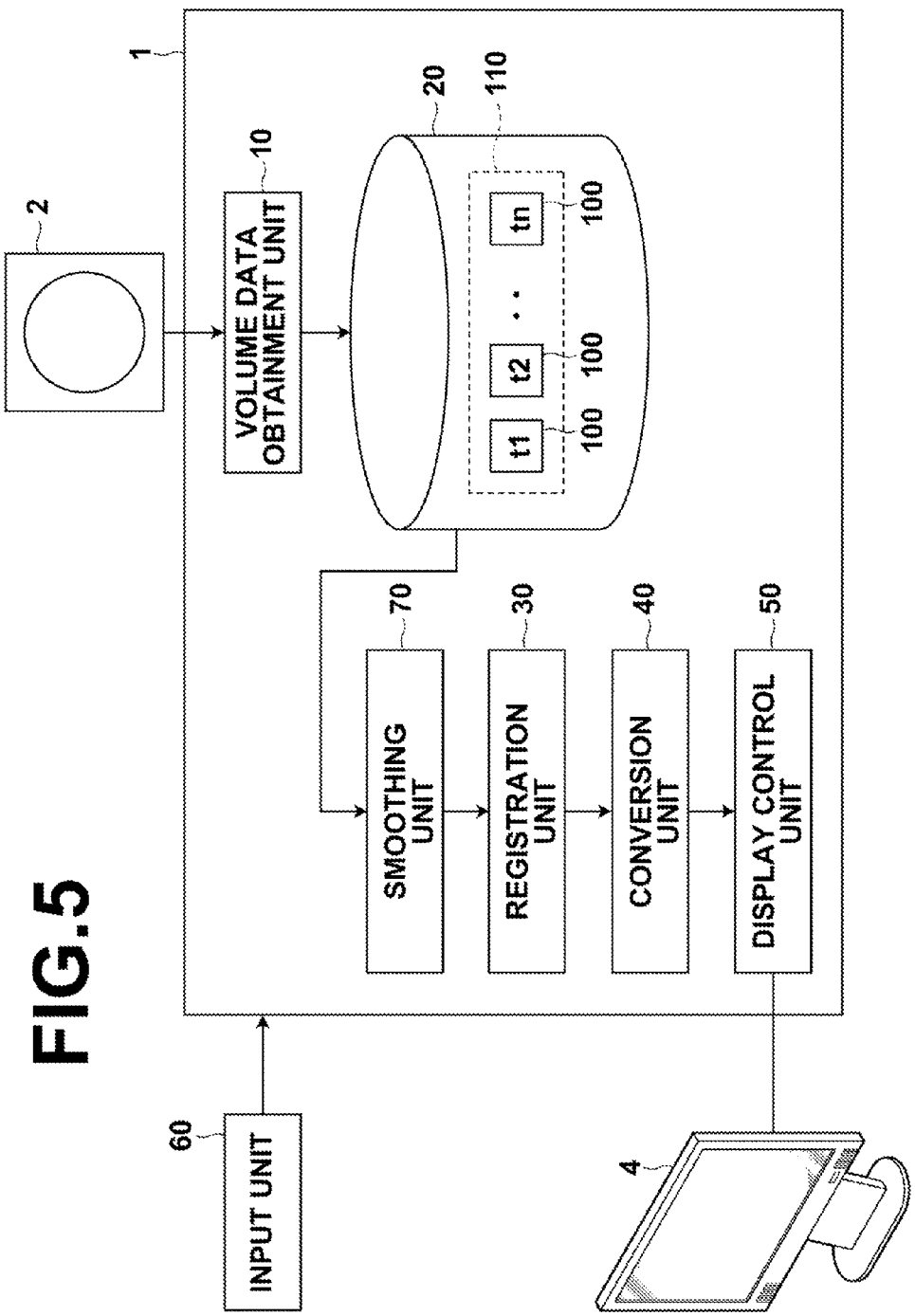
FIG. 5 is a schematic block diagram illustrating the configuration of a medical image conversion apparatus according to a second embodiment of the present invention.

Further, as in a second embodiment illustrated in FIG. 5, a smoothing unit 70 may be provided to perform smoothing on each set of three-dimensional volume data 100 before performing registration of voxel positions between the sets of three-dimensional value data 100. Specifically, smoothing should be performed on each set of three-dimensional volume data 100 by calculating an average of signal values at respective voxel positions of the three-dimensional volume data 100 by using a smoothing filter of a predetermined size (for example, 3×3×3). Accordingly, it is possible to reduce an influence of noise included in the three-dimensional volume data 100 when registration is performed. Therefore, more accurate registration becomes possible.

In the aforementioned embodiment, a case of displaying a three-dimensional volume data group 110 of a heart in time series by VR was described. Needless to say, the present invention is applicable to a case in which two-dimensional images representing a cross section of a heart on a slice surface at the same position of each set of three-dimensional volume data 100 is extracted from the sets of three-dimensional volume data 100, respectively, and the extracted two-dimensional images are displayed in time series after converting the density and/or the color of the extracted two-dimensional images. Further, the time series images are not limited to the three-dimensional volume data 100. Alternatively, an image group composed of a series of images obtained by plain roentgenography with predetermined time intervals may be used as the time series images.

Figure 6:
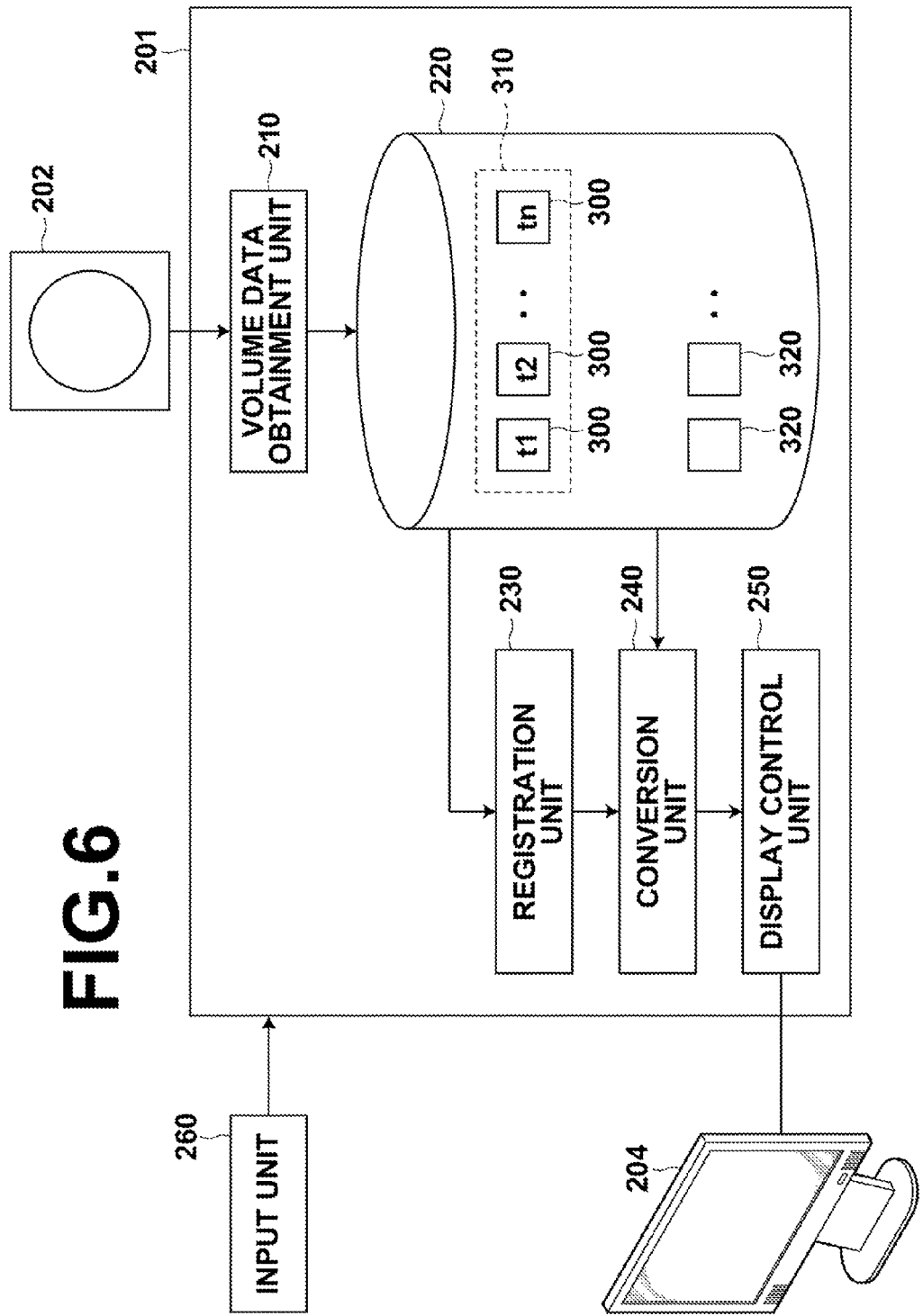
FIG. 6 is a schematic block diagram illustrating the configuration of a medical image conversion apparatus according to a third embodiment of the present invention.

Next, a third embodiment of the present invention will be described. FIG. 6 is a schematic block diagram illustrating the configuration of a medical image conversion apparatus according to the third embodiment of the present invention. A medical image conversion apparatus 201 according to the third embodiment includes a volume data obtainment unit 210, a storage unit 220, a registration unit 230, a conversion unit 240, a display control unit 250, and an input unit 260 corresponding to the volume data obtainment unit 10, the storage unit 20, the registration unit 30, the conversion unit 40, the display control unit 50 and the input unit 60 in the medical image conversion apparatus 1 according to the first embodiment.

The volume data obtainment unit 210 has a communication interface function for obtaining a three-dimensional volume data group 310 composed of plural sets of three-dimensional volume data 300 obtained by imaging a specific region of a subject with predetermined time intervals Δt by a modality 202, such as a CT apparatus or an MRI apparatus. The three-dimensional volume data group 310 is sent from the modality 202 through LAN. In the third embodiment, it is assumed that the specific region is a liver, and that a three-dimensional volume data group 310 representing the flow of a contrast agent is obtained by administering the contrast agent to a subject, and by imaging the abdomen of the subject by a CT apparatus.

Here, the three-dimensional volume data 300 are obtained by placing one on another two-dimensional tomographic image data of the liver to be diagnosed that have been sequentially obtained along a direction perpendicular to a cross section. In the third embodiment, the three-dimensional volume data 300 are obtained by placing, one on another, plural tomographic images obtained by a modality 202, such as a CT apparatus or an MRI apparatus. Volume data obtained by using the CT apparatus store an absorption amount of X-rays for each voxel (in other words, a voxel position). In the volume data, a single signal value (when imaging is performed by a CT apparatus, a value representing an absorption amount of X-rays) has been provided for each voxel position.

The three-dimensional volume data group 310 is composed of a series of three-dimensional volume data 300 obtained, for example, by imaging a subject in different phases t1, t2 . . . to with predetermined time intervals Δt.

Here, supplementary information defined by DICOM (Digital Imaging and Communications in Medicine) standard is attached to the three-dimensional volume data 300.

The storage unit 220 is a large-capacity storage device, such as a hard disk. A three-dimensional volume data group 310 is stored in the storage unit 220. The storage unit 220 stores plural three-dimensional volume data groups 310 of different subjects (in other words, different patients), or of the same subject imaged at different points of time. Further, a color template 320, which will be described later, is also stored in the storage unit 220. Plural color templates are prepared in advance for regions to be extracted from the three-dimensional volume data 300 for VR display, and stored in the storage unit 220.

The registration unit 230 performs registration of corresponding voxel positions in a liver part for each set of three-dimensional volume data 300 between sets of three-dimensional volume data 300 in a manner similar to the registration unit 30 in the first embodiment.

Figure 7:
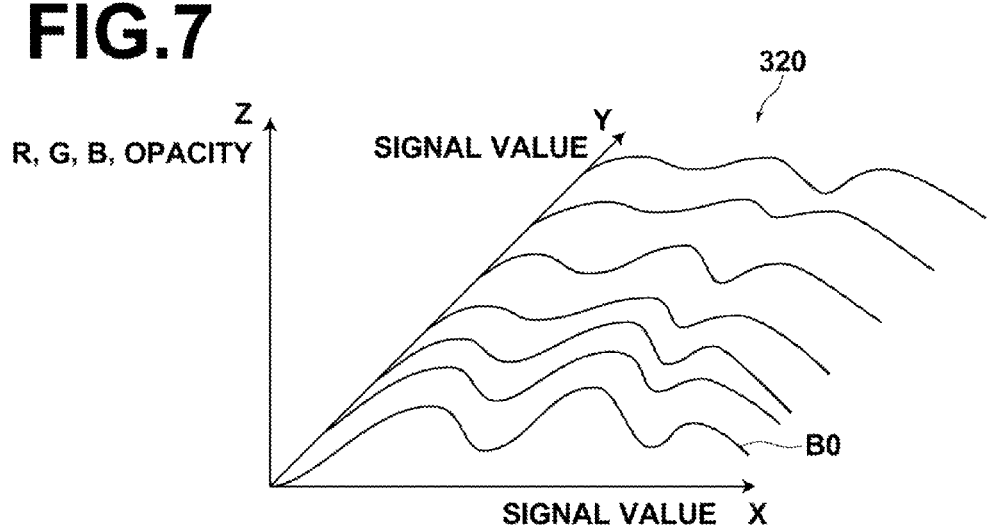
FIG. 7 is a diagram illustrating a color template for converting three-dimensional volume data in the third embodiment.

The conversion unit 240 converts a signal value at each voxel position of the three-dimensional volume data 300 into a display voxel value to display an image by volume rendering (VR). FIG. 7 is a diagram illustrating a color template for converting the three-dimensional volume data 300. Plural color templates 320 are prepared in advance for regions to be extracted from the three-dimensional volume data 300 for VR display, and stored in the storage unit 220. In the third embodiment, it is assumed that a color template 320 for displaying a liver by VR is selected. As illustrated in FIG. 7, in the third embodiment, the color template 320 is composed of a two-dimensional lookup table in which a first signal value that is used as a base is set on first axis X, and a second signal value that is obtained by changing the first signal value is set on second axis Y, and colors (R, G, B) and opacities for the first signal value and the second signal value are set on third axis Z. FIG. 7 illustrates only a color template. However, actually, four color templates are provided for the colors of R, G and B and opacity, respectively.

Next, generation of a two-dimensional lookup table will be described. When a CT image is used, a signal value is represented by the unit of HU (Hounsfield unit), and the HU is a fixed value for each tissue. For example, when a region to be imaged is an abdomen as in this embodiment, signal values are fixed values for tissues, such as a liver, a spleen and blood vessels. In other words, the signal values differ depending on the tissue. Further, the manner of change in the signal value of each tissue by administration of a contrast agent is known. When MRI images are obtained, signal values differ depending on an imaging apparatus. However, it is possible to make the images have fixed signal values for each tissue by correcting a difference in the signal values between the apparatuses. Therefore, one-dimensional base lookup table B0, which is a base, is generated by using signal values of the three-dimensional volume data 300 before administration of a contrast agent. In the one-dimensional base lookup table B0, signal values of the three-dimensional volume data 300 are set on first axis X, and a color (R, G, B) and an opacity for each tissue are set on third axis Z. Further, signal values that change by administration of a contrast agent or the like are set on second axis Y. Further, a color and an opacity based on a change in a signal value are set two-dimensionally in the direction of third axis Z with respect to a plane defined by the first and second axis X, Y. Accordingly, it is possible to generate a two-dimensional lookup table.

The conversion unit 240 converts a signal value at each voxel position of the three-dimensional volume data 300 into a display voxel value composed of R, G, B and an opacity with reference to the color template 320. In this case, the conversion unit 240 selects a base phase B, which is a base, from phases of plural sets of three-dimensional volume data 300. With respect to the three-dimensional volume data 300 in the base phase B (hereinafter, referred to as base three-dimensional volume data 330), the conversion unit 240 converts a signal value at each voxel position to a display voxel value composed of a color and an opacity by using the part of base lookup table B0 in the color template 320. Meanwhile, with respect to the three-dimensional volume data 300 in phases other than the base phase, the conversion unit 240 plots a signal value at each voxel position to second axis Y of the color template 320, and plots a signal value at a corresponding voxel position in the base three-dimensional volume data 330 to first axis X. Further, the conversion unit 240 obtains a color and an opacity corresponding to the plotted values on third axis Z. Accordingly, the conversion unit 240 converts the signal value into the display voxel value composed of the color and the opacity.

Figure 8:
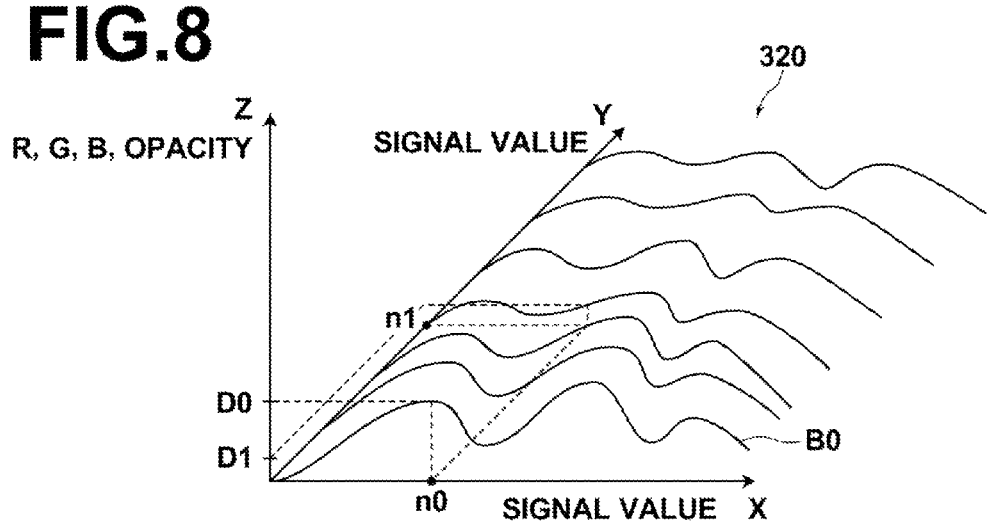
FIG. 8 is a diagram for explaining conversion into display voxel values.

The process will be specifically described with reference to FIG. 8. When a signal value at a certain voxel position (target voxel position) in the base three-dimensional volume data 330 is n0, the signal value at the target voxel position is converted into display voxel value D0 with reference to the color template 320. When a signal value at a corresponding voxel position, which corresponds to the target voxel position, changes to n1 in the three-dimensional volume data 300 in different phases, a signal value at the corresponding voxel position is converted into display voxel value D1 with reference to the color template 320.

Here, selection of the base phase B should be performed by selecting a predetermined phase, for example, such as a first phase, or a middle phase, or a last phase in phases of the three-dimensional volume data group 310, and a phase when lowest-noise three-dimensional volume data 300 were obtained. Alternatively, selection of a phase, as the base phase B, may be received by an input from the input unit 260. In the third embodiment, a change in signal values by administration of a contrast agent is observed. Therefore, it is desirable to select the first phase as the base phase B, because the effect of a contrast agent does not appear in the first phase, and the same tissue has the same signal value, and different tissues have different signal values.

Further, the conversion unit 240 converts a signal value at each voxel position of all the sets of three-dimensional volume data 300 into a display voxel value with reference to the color template 320. Accordingly, the three-dimensional volume data 300 represent a VR image obtained by extracting the liver.

The display control unit 250 displays, in time series, a VR image represented by a series of converted three-dimensional volume data 300 on the display 204. In the third embodiment, a liver during administration of a contrast agent is displayed. Therefore, a flow of the contrast agent in the liver is displayed on the display 204.

The input unit 260 is composed of a known input device, such as a keyboard and a mouse.

Figure 9:
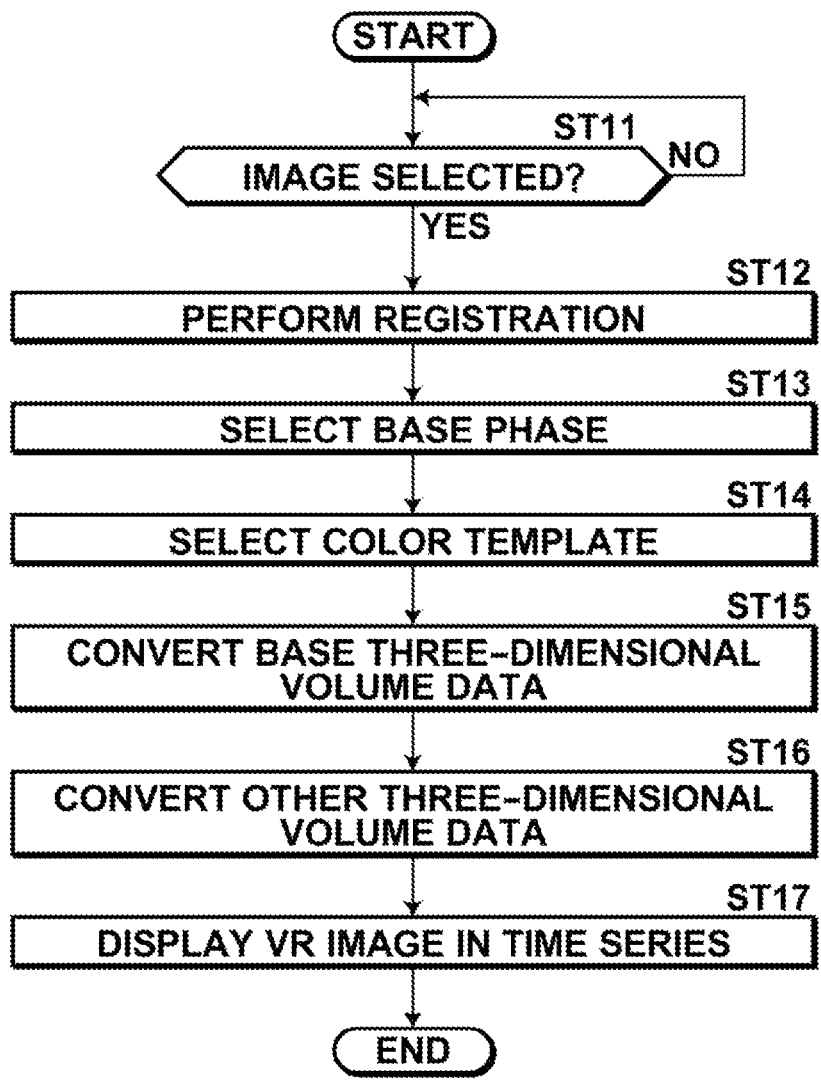
FIG. 9 is a flow chart illustrating processing in the third embodiment.

Next, processing performed in the third embodiment will be described. FIG. 9 is a flow chart illustrating processing performed in the third embodiment. It is assumed that the three-dimensional volume data group 310 has been obtained by the volume data obtainment unit 210, and stored in the storage unit 220. Further, it is assumed that plural color templates 320 have been stored in the storage unit 220. When a three-dimensional image to be displayed is selected by operation of the input unit 260 by an operator (step ST11, YES), the registration unit 230 reads out a three-dimensional volume data group 310 corresponding to the selected three-dimensional image from the storage unit 220, and performs registration of voxel positions between sets of three-dimensional volume data 300 constituting the three-dimensional volume data group 310 (step ST12). Accordingly, voxel positions are correlated to each other between the sets of three-dimensional volume data 300.

Further, the conversion unit 240 selects base phase B (step ST13), and selects a color template 320 used for conversion (step ST14). Next, the conversion unit 240 converts a signal value at each voxel position in the base three-dimensional volume data 330 in the base phase B into a display voxel value with reference to the part of the base lookup table B0 included in the color template 320 (step ST15). Further, the conversion unit 240 converts a signal value at each voxel position in the three-dimensional volume data 300 other than the base three-dimensional volume data 330 to a display voxel value based on the selected color template 320 (step ST16). Further, the display control unit 250 displays a VR image represented by the converted three-dimensional volume data 300 on the display 204 in time series (step ST17), and processing ends.

As described above, in the third embodiment, the color template 320 composed of a two-dimensional lookup table in which a first signal value, which is a base, is set on first axis X, and a second signal value obtained by changing the first signal value is set on second axis Y, and a color (R, G, B) and an opacity for the first and second signal values are set on third axis Z is used, and a signal value at each voxel position of the three-dimensional volume data 300 is converted into a display voxel value based on the base three-dimensional volume data 330. Therefore, even if the signal values of tissues change in the same manner as time passes, if signal values are different from each other in the base three-dimensional volume data 300, it is possible to convert the signal values of the tissues to different display voxel values by selecting an appropriate color template 320. Further, even if signal values of the same tissue differ from each other, the signal values of the same tissue should be originally the same. Therefore, it is possible to display the same tissue at the same display voxel values by choosing, as the base phase B, a phase in which the signal values of the same tissue are the same. Therefore, according to the third embodiment, accurate diagnosis is possible by using the three-dimensional volume data group 310 displayed in time series.

Figure 10:
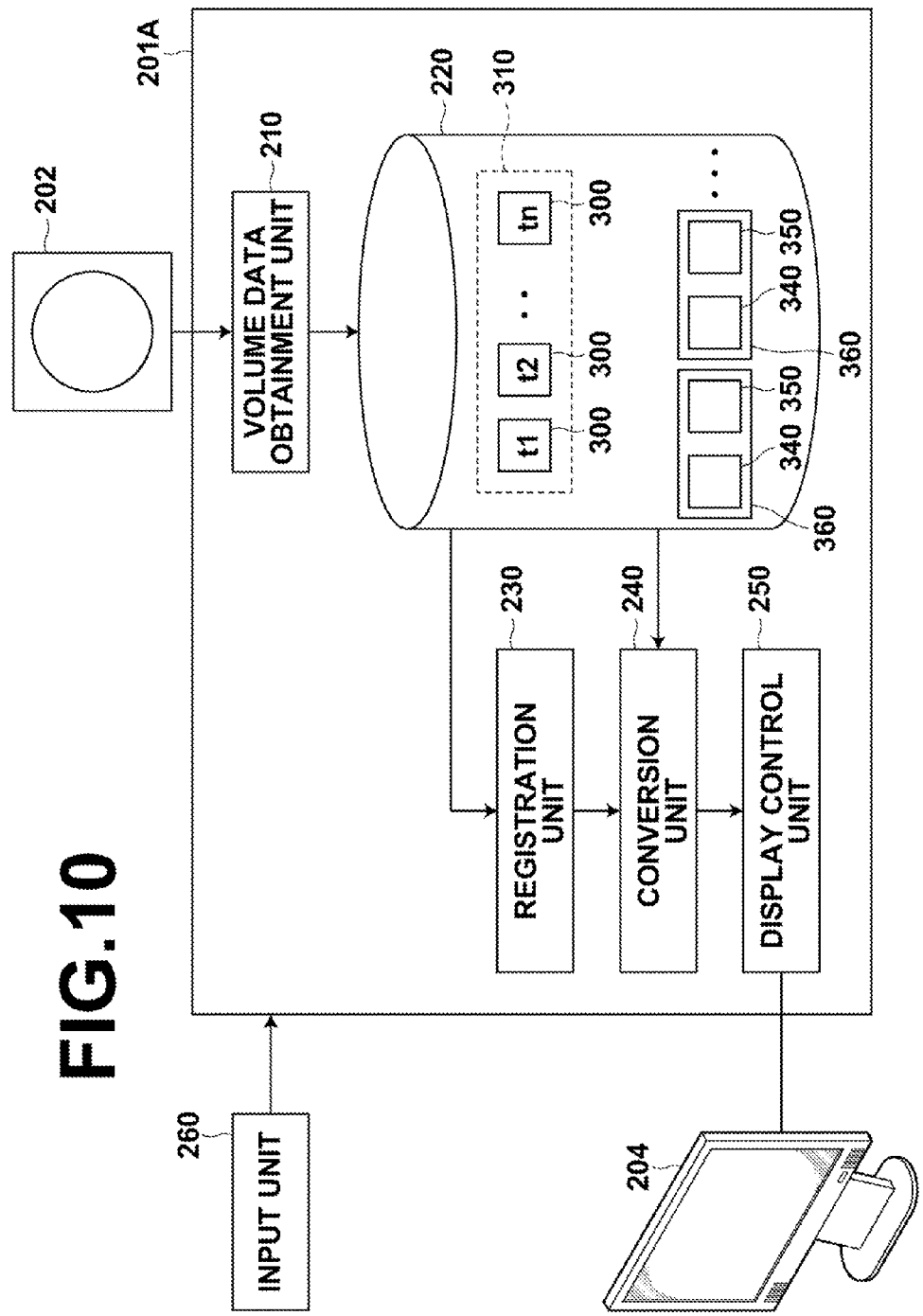
FIG. 10 is a schematic block diagram illustrating the configuration of a medical image conversion apparatus according to a fourth embodiment of the present invention.

Next, a fourth embodiment of the present invention will be described. FIG. 10 is a schematic block diagram illustrating the configuration of a medical image conversion apparatus according to the fourth embodiment of the present invention. In the fourth embodiment, the same reference numerals will be assigned to the same elements as those of the third embodiment, and detailed descriptions will be omitted. A medical image conversion apparatus 201A in the fourth embodiment differs from the third embodiment in that a pair color template 360 composed of a base color template 340, which is composed of a one-dimensional lookup table, and its difference color template 350 is stored in the storage unit 220 instead of the color template 320 composed of a two-dimensional lookup table, and in that the conversion unit 240 converts signal values of the three-dimensional volume data 300 into display voxel values by using the pair color template 360. Here, plural pair color templates 360 are prepared in advance for regions to be extracted from the three-dimensional volume data 300 for VR display. It is assumed that a pair color template 360 for displaying a liver by VR is selected also in the fourth embodiment.

FIGS. 11A and 11B are diagrams illustrating a base color template and a difference template. As illustrated in FIGS. 11A and 11B, the base color template 340 is a one-dimensional lookup table in which signal values of the three-dimensional volume data 300 are set on the horizontal axis, and a color (R, G, B) and an opacity of the three-dimensional volume data 300 are set on the vertical axis. The difference color template 350 is a one-dimensional lookup table in which a variation in signal values is set on the horizontal axis, and a variation in the color and the opacity is set on the vertical axis. In FIGS. 11A and 11B, only a base color template and a difference template are illustrated. Actually, a pair color template 360 composed of four base color templates and four difference templates for the colors of R, G, B and the opacity, respectively, are prepared.

The conversion unit 240 selects a base phase B, which is a base, from phases of the plural sets of three-dimensional volume data 300. Further, with respect to the base three-dimensional volume data 330 in the base phase B, the conversion unit 240 converts a signal value at each voxel position into a display voxel value composed of a color and an opacity with reference to the base color template 340. Meanwhile, with respect to three-dimensional volume data 300 in phases other than the base phase, first, the conversion unit 240 calculates, as variation ΔS in signal values, a difference value (S0−SB) between signal value S0 at each voxel position in the three-dimensional volume data 300 and signal value SB at a corresponding voxel position in the base three-dimensional volume data 330. Further, the conversion unit 240 calculates variation ΔD of a display voxel value (D10) at a corresponding voxel position in the base three-dimensional volume data 330 with reference to the difference color template 350. Then, the conversion unit 240 corrects display voxel value D10 at the corresponding voxel position in the base three-dimensional volume data 330, using the calculated variation ΔD of the display voxel value, and calculates a corrected display voxel value (D10+ΔD). Further, the conversion unit 240 converts signal value S0 at each voxel position in the three-dimensional volume data 300 into a corrected display voxel value (D10+ΔD).

Specifically, when a signal value is converted into an opacity, if a signal value at each voxel position in the three-dimensional volume data 300 does not change from a signal value at a corresponding voxel position in the base three-dimensional volume data 330, the signal value is converted in such a manner that the opacity does not change. Meanwhile, signal values are converted in such a manner that a voxel position at which a signal value increases becomes opaquer and that a voxel position at which a signal value decreases becomes more transparent. When the signal value is converted into the color of R, if a signal value at each voxel position in the three-dimensional volume data 300 does not change from a signal value at a corresponding voxel position in the base three-dimensional volume data 330, the signal value is converted in such a manner that the degree of red does not change. Meanwhile, signal values are converted in such a manner that the degree of red becomes higher at a voxel position at which a signal value increases and that the degree of red becomes lower at a voxel position at which a signal value decreases.

In the above descriptions, a difference value (S0−SB) between signal value S0 at each voxel position in the three-dimensional volume data 300 and signal value SB at a corresponding voxel position in the base three-dimensional volume data 330 is calculated as variation ΔS in signal values. However, the variation ΔS in signal values is not limited to the difference value (S0−SB) as long as the value is an index representing a variation in signal values between the voxel positions. For example, the absolute value of the variation ΔS in signal values, the logarithm of the variation ΔS in signal values, or the like may be used instead of the difference value (S0−SB). In this case, the difference color template 350 should be generated to define a relationship between the absolute value of the difference value, or the logarithm of the difference value, or the like and a variation in the display voxel value.

Further, a variation in signal values in plural phases may be calculated, and the variation in signal values may be plotted as illustrated in FIG. 12. Further, a point at which the gradient of the variation in signal values becomes the highest in the plot may be obtained, and the difference color template 350 may be corrected so that a variation in the display voxel value at the point is higher than variations at other points. Accordingly, a variation in display voxel values becomes large in apart in which a variation in signal values is large. Therefore, it becomes possible to easily recognize a change.

Figure 13:
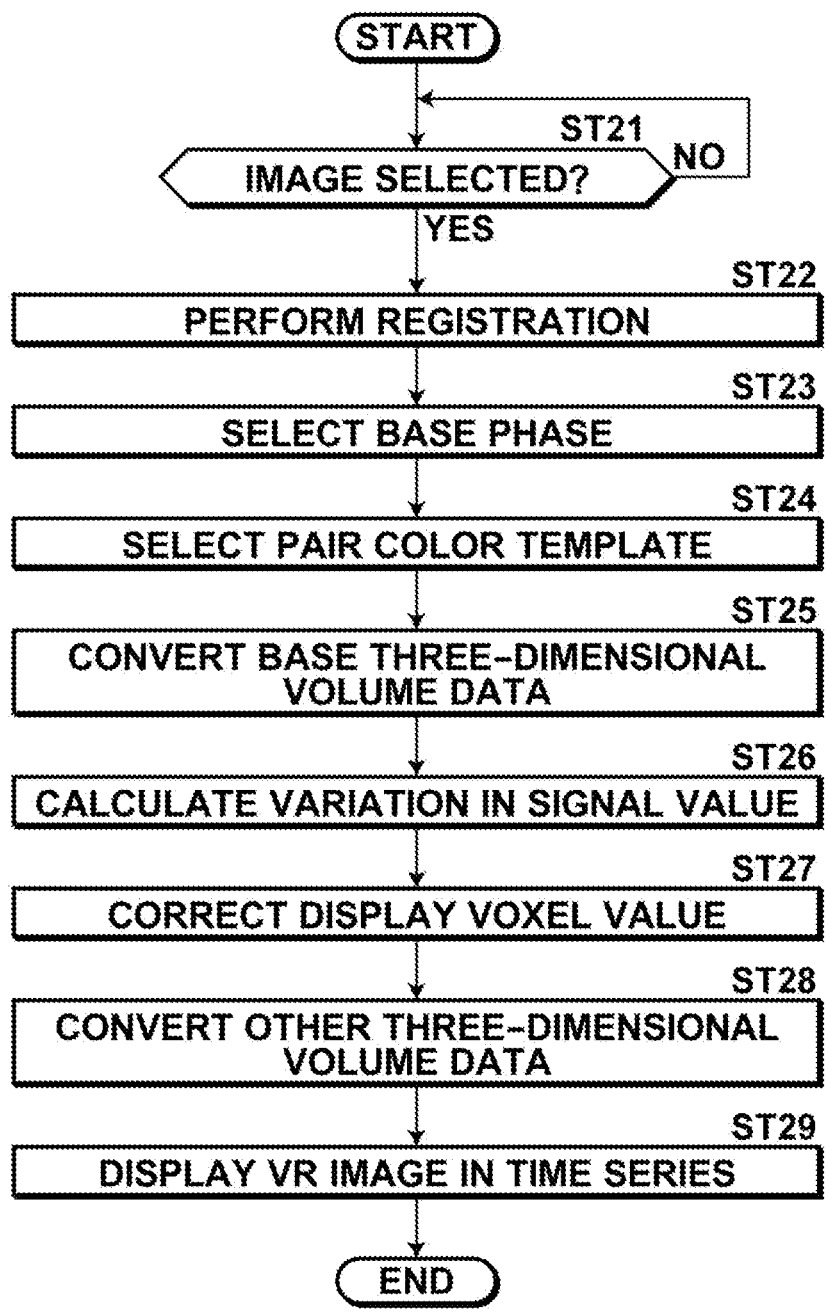
FIG. 13 is a flow chart illustrating processing performed in the fourth embodiment.

Next, processing performed in the fourth embodiment will be described. FIG. 13 is a flow chart illustrating processing performed in the fourth embodiment. Here, it is assumed that the three-dimensional volume data group 310 has been obtained by the volume data obtainment unit 210, and stored in the storage unit 220. Further, it is assumed that plural pair color templates 360 have been stored in the storage unit 220. When a three-dimensional image to be displayed is selected by operation of the input unit 260 by an operator (step ST21, YES), the registration unit 230 reads out a three-dimensional volume data group 310 corresponding to the selected three-dimensional image from the storage unit 220, and performs registration of voxel positions between sets of three-dimensional volume data 300 constituting the three-dimensional volume data group 310 (step ST22). Accordingly, voxel positions are correlated to each other between the sets of three-dimensional volume data 300.

Further, the conversion unit 240 selects base phase B (step ST23), and selects a pair color template 360 used for conversion (step ST24). Next, the conversion unit 240 converts a signal value at each voxel position in the base three-dimensional volume data 330 in the base phase B into a display voxel value with reference to the base color template 340 included in the pair color template 360 (step ST25). Further, with respect to all the sets of three-dimensional volume data 300 other than the base phase, a difference value between a signal value at each voxel position and a signal at a corresponding voxel position in the base three-dimensional volume data 330 is calculated as a variation in signal values (step ST26). Further, a display voxel value corresponding to each voxel position in the base three-dimensional volume data 330 is corrected based on a variation in signal values with reference to the difference color template 350 (step ST27). Further, a signal value at each voxel position in the three-dimensional volume data 300 other than the base three-dimensional volume data 330 is converted into a corrected display voxel value (step ST28). Further, the display control unit 250 displays a VR image represented by the converted three-dimensional volume data 300 on the display 204 in time series (step ST29), and processing ends.

As described above, in the fourth embodiment, a signal value at each voxel position in the base three-dimensional volume data 330 is converted into a display voxel value with reference to the base color template 340. With respect to other three-dimensional volume data 300, a display voxel value is corrected based on a variation between a signal value at each voxel position and a signal value at a corresponding voxel position in the base three-dimensional volume data 330 with reference to the difference color template 350. A signal value at each voxel position is converted so that the signal value becomes a corrected display voxel value. Therefore, a change in signal values in each set of the three-dimensional volume data 300 is certainly reflectable in a change in display voxel values. Hence, when a phase in which the same tissue has the same signal value and different tissues have different signal values is used as base phase B, it is possible to certainly recognize a change in signal values in the three-dimensional volume data group 310 that is displayed in time series.

In the fourth embodiment, the pair color template 360 composed of the base color template 340 and the difference color template 350 is used. Instead of the difference color template 350, a variation in display voxel values may be calculated by using an operation equation in which a variation in signal values is an input and a variation in display voxel values is an output. In this case, only the base color template 340 is stored in the storage unit 220.

In the fourth embodiment, a signal value at each voxel position in the three-dimensional volume data 300 other than the base three-dimensional volume data 330 is converted into a corrected display voxel value. Alternatively, a signal value at each voxel position of the base three-dimensional volume data 330 may be converted into a corrected display voxel value. Next, this will be described as a fifth embodiment. In the firth embodiment, only processing is different from the fourth embodiment. Therefore, detailed descriptions of the apparatus will be omitted.

Figure 14:
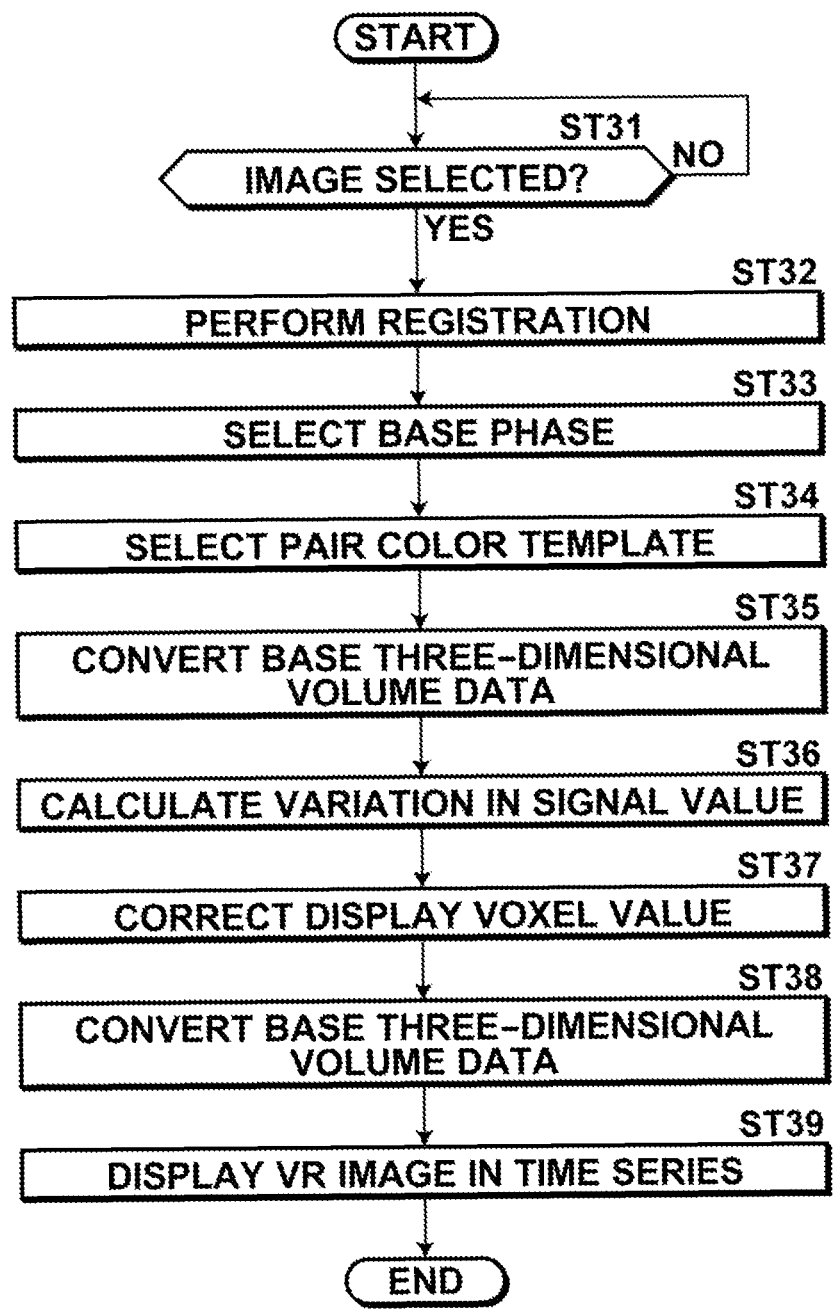
FIG. 14 is a flow chart illustrating processing performed in the fifth embodiment.

FIG. 14 is a flow chart illustrating processing performed in the fifth embodiment. It is assumed that the three-dimensional volume data group 310 has been obtained by the volume data obtainment unit 210, and stored in the storage unit 220. Further, it is assumed that plural pair color templates 360 are stored in the storage unit 220. When a three-dimensional image to be displayed is selected by operation of the input unit 260 by an operator (step ST31, YES), the registration unit 230 reads out a three-dimensional volume data group 310 corresponding to the selected three-dimensional image from the storage unit 220, and performs registration of voxel positions between sets of three-dimensional volume data 300 constituting the three-dimensional volume data group 310 (step ST32). Accordingly, voxel positions are correlated to each other between the sets of three-dimensional volume data 300.

Further, the conversion unit 240 selects base phase B (step ST33), and selects a pair color template 360 used for conversion (step ST34). Next, the conversion unit 240 converts a signal value at each voxel position in the base three-dimensional volume data 330 in the base phase B into a display voxel value with reference to the base color template 340 included in the pair color template 360 (step ST35). Further, with respect to all the sets of three-dimensional volume data 300 other than the base phase, a difference value between a signal value at each voxel position and a signal at a corresponding voxel position in the base three-dimensional volume data 330 is calculated as a variation in signal values (step ST36). Further, a display voxel value corresponding to each voxel position in the base three-dimensional volume data 330 is corrected based on a variation in signal values with reference to the difference color template 350 (step ST37). Further, a signal value at each voxel position in the base three-dimensional volume data 330 is converted into a corrected display voxel value for each set of corresponding three-dimensional volume data 300 (step ST38).

In this case, plural sets of base three-dimensional volume data 330 in which signal values have been converted into corrected display voxel values are generated in such a manner to correspond to three-dimensional volume data 300 other than the base three-dimensional volume data 330. Further, the display control unit 250 displays a VR image represented by the converted three-dimensional volume data 300 on the display 204 in time series (step ST39), and processing ends. In the fifth embodiment, a VR image generated based on the base three-dimensional volume data 330 is displayed in time series in such a manner that display voxel values change in the same phase as the three-dimensional volume data 300 based on which the corrected display voxel value was obtained.

Accordingly, it is possible to certainly recognize a change in signal values in the three-dimensional volume data group 310 displayed in time series also in the fifth embodiment.

In the third through fifth embodiments, a three-dimensional volume data group of an abdomen is used. Alternatively, a three-dimensional volume data group of a head or a neck may be used. In this case, a VR image is four-dimensionally displayed in such a manner that a change in the head or the neck appears by administration of a contrast agent to blood vessels.

Figure 15:
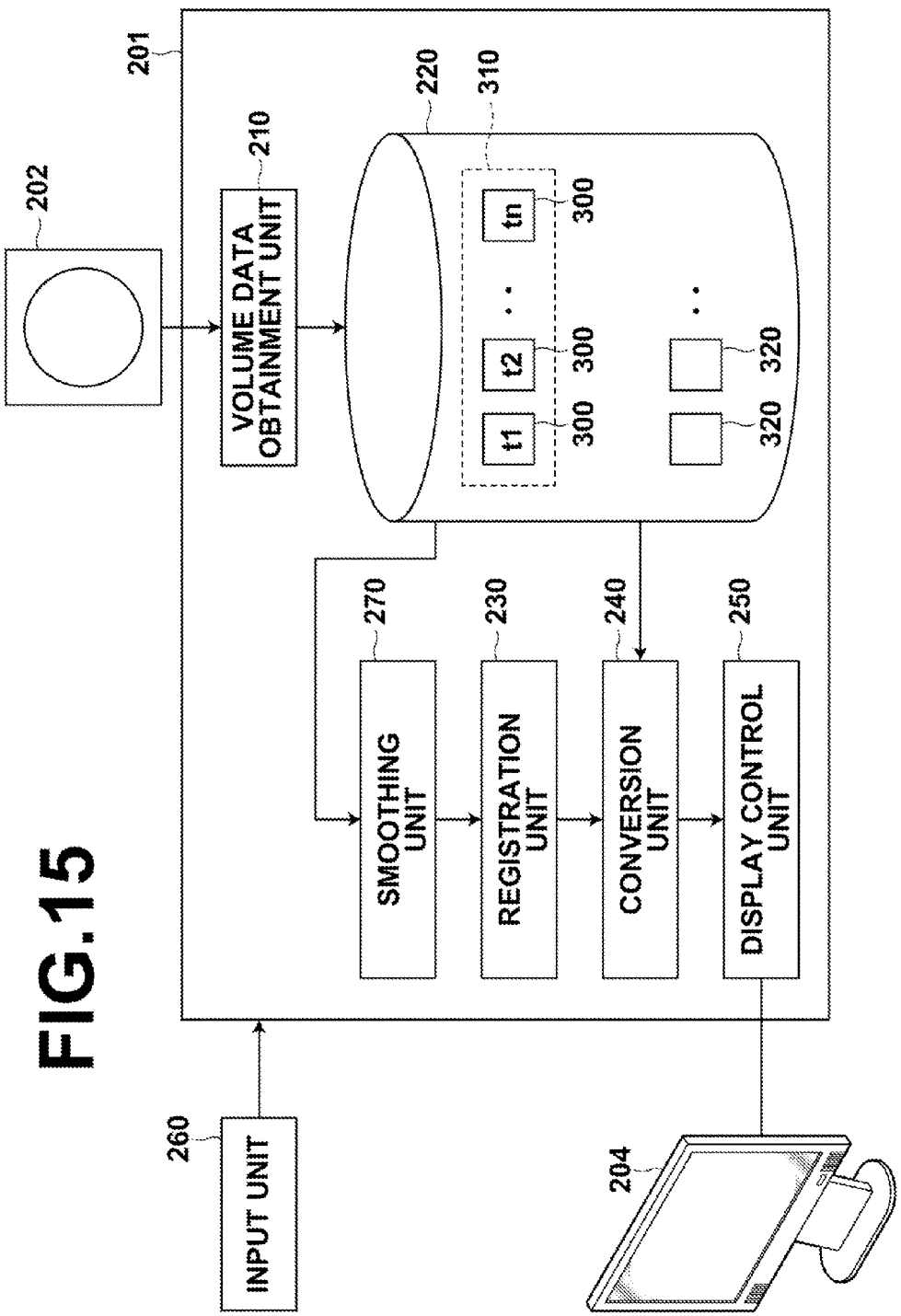
FIG. 15 is a schematic block diagram illustrating processing performed in a sixth embodiment.

As illustrated as a sixth embodiment in FIG. 15, a smoothing unit 270 may be provided in the third embodiment. Smoothing may be performed on each set of three-dimensional volume data 300 before performing registration of voxel positions between the sets of three-dimensional volume data 300. Specifically, smoothing should be performed on each set of three-dimensional volume data 300 by calculating an average of signal values at voxel positions in the three-dimensional volume data 300 by using a smoothing filter of a predetermined size (for example, 3×3×3). Accordingly, it is possible to reduce an influence of noise included in the three-dimensional volume data 300 when registration is performed. Therefore, more accurate registration becomes possible. Similarly, the smoothing unit 270 may be provided also in the fourth and fifth embodiments.

In the third through sixth embodiments, the registration unit 230 performs registration of sets of three-dimensional volume data 300. However, motion of a region, such as the abdomen or the head and the neck, is small, or the region does not substantially move. Therefore, with respect to the three-dimensional volume data 300 of such regions, signal values may be converted without performing registration.

In the third through sixth embodiments, a case in which the three-dimensional volume data group 310 of the abdomen is displayed by VR in time series was described. Needless to say, the present invention is applicable to a case in which a two-dimensional image representing a cross section of the abdomen on a slice surface at the same position of each set of three-dimensional volume data 300 is extracted from the sets of three-dimensional volume data 300, respectively, and the extracted two-dimensional images are displayed in time series after converting the density and/or the color of the extracted two-dimensional images. Further, the time series image is not limited to the three-dimensional volume data 300. Alternatively, an image group composed of a series of images obtained by plain roentgenography with predetermined time intervals may be used.

For example, the present invention may be applied to a case of sequentially displaying plural sets of three-dimensional volume data obtained by imaging by a CT apparatus using plural kinds of X-rays of different energies, as disclosed in Japanese Unexamined Patent Publication No. 2009-178493. In this case, a display voxel value may be changed based on a change in a signal value caused by a change in the energy of radiation used for imaging by converting a signal value of each of plural sets of three-dimensional volume data of different energies into a display voxel value in a manner similar to the third through sixth embodiments. Accordingly, it is possible to sequentially display the three-dimensional volume data based on a change in the energy of X-rays during imaging.

The invention claimed is:

1. A medical image conversion apparatus comprising:
   an image obtainment unit that obtains a series of temporal medical images about a specific organ in different phases;
   a registration unit that performs registration of corresponding voxel positions of the specific organ in each of the temporal medical images of the series of temporal medical images to thereby register the corresponding voxel positions of the specific organ between each of the temporal medical images of the series of temporal medical images; and
   a conversion unit that, from the series of temporal medical images of the specific organ that includes a base medical image and additional medical images, the additional medical images including at least a first medical image and a second medical image,
   i) for each of the additional medical images, converts signal values at each of the registered voxel positions of the specific organ in each of the additional medical images of the series of temporal medical images into a voxel value at a respective corresponding registered voxel position of the specific organ in the base medical image to thereby form a converted series of temporal medical images, where the signal value at each corresponding registered voxel position of the specific organ, includes a same voxel value in the base medical image and each of the additional medical images, and
   ii) further converts the signal values at each of the corresponding registered voxel positions in the additional medical images of the converted series of temporal medical images into a same display voxel value as in the base medical image such that each respective one of the corresponding registered voxel positions of the specific organ in the base medical image and the additional medical images of the converted series of temporal medical images have a respective same display voxel value.

2. A medical image conversion apparatus, as defined in claim 1, the apparatus further comprising:
   a smoothing unit that performs smoothing of the series of time series images before performing registration.

3. A medical image conversion apparatus, as defined in claim 1, the apparatus further comprising:
   a display unit that displays, in time series, the series of time series images after the conversion.

4. A medical image conversion apparatus, as defined in claim 1, wherein the time series medical images are three-dimensional medical images.

5. A medical image conversion apparatus, as defined in claim 1, wherein the specific organ is a heart and/or a lung.

6. A medical image conversion method comprising the steps of:
   obtaining a series of temporal medical images about a specific organ in different phases;
   performing registration of voxel positions of the specific organ in the series of temporal medical images between each of temporal medical images of the series of temporal medical images; and
   wherein the series of temporal medical images of the specific organ that includes a selected base medical image and additional medical images,
   converting signal values at voxel positions of the specific organ in the additional medical images of temporal medical images into a voxel value at a corresponding voxel position of the specific organ in the base medical image to thereby form a converted series of temporal medical images, and further converting the signal values at the corresponding voxel positions of the specific organ in the additional medical images in the converted series of temporal medical images into a same display voxel value of the base medical image of the converted series of temporal medical images such that each respective one of the corresponding registered voxel positions of the specific organ in the base medical image and the additional medical images of the converted series of temporal medical images have a respective same display voxel value.

7. A non-transitory computer-readable recording medium storing therein a program for causing a computer to execute a medical image conversion method, the program comprising the procedures of:

obtaining a series of temporal medical images about a specific organ in different phases;

performing registration of voxel positions of the specific organ in the series of temporal medical images between each of temporal medical images of the series of temporal medical images; and wherein the series of temporal medical images of the specific organ that includes a selected base medical image and additional medical images, converting signal values at voxel positions of the specific organ in the additional medical images of temporal medical images into a voxel value at a corresponding voxel position of the specific organ in the base medical image to thereby form a converted series of temporal medical images, and further converting the signal values at the corresponding voxel positions of the specific organ in the additional medical images in the converted series of temporal medical images into a same display voxel value of the base medical image of the converted series of temporal medical images such that each respective one of the corresponding registered voxel positions of the specific organ in the base medical image and the additional medical images of the converted series of temporal medical images have a respective same display voxel value.

8. A medical image conversion apparatus comprising:

an image obtainment unit that obtains a series of a plurality of medical images about a specific region; a conversion unit that converts, with respect to a target medical image to be converted of the series of medical images, a signal value at each voxel position in the target medical image into a display voxel value based on a variation between the signal value and a signal value at each corresponding voxel position in a base medical image; and a storage unit that stores a color template defining a relationship among a first signal value that is used as a base, a second signal value that is obtained by changing the first signal value, and display voxel values for the first and second signal values, wherein the conversion unit converts, based on the base medical image, the signal value at each voxel position in the target medical image into the display voxel value with reference to the color template.

9. A medical image conversion apparatus, as defined in claim 8, wherein the conversion unit converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the target medical image into the corrected display voxel value.

10. A medical image conversion apparatus, as defined in claim 8, wherein the conversion unit converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the base medical image into the corrected display voxel value.

11. A medical image conversion apparatus, as defined in claim 10, the apparatus further comprising:

a display unit that displays, in time series, the base medical image after the conversion in such a manner to be matched with the phase of the target medical image based on which the corrected display voxel value has been obtained when the medical images have been obtained in time series.

12. A medical image conversion apparatus, as defined in claim 8, the apparatus further comprising:

a display unit that displays, in time series, the series of medical images after the conversion when the medical images have been obtained in time series.

13. A medical image conversion apparatus, as defined in claim 8, wherein the series of medical images are obtained by performing radiography using a plurality of kinds of radiation of different energy from each other.

14. A medical image conversion apparatus, as defined in claim 8, the apparatus further comprising:

a registration unit that performs registration of voxel positions in the series of medical images between the series of medical images.

15. A medical image conversion apparatus, as defined in claim 14, the apparatus further comprising:

a smoothing unit that performs smoothing of the series of medical images before performing registration.

16. A medical image conversion apparatus, as defined in claim 8, wherein the medical images are three-dimensional medical images.

17. A medical image conversion apparatus, as defined in claim 8, wherein the medical images are obtained by imaging using a contrast agent.

18. A medical image conversion method comprising the steps of:

obtaining a series of a plurality of medical images about a specific region;

converting, with respect to a target medical image to be converted of the series of medical images, a signal value at each voxel position in the target medical image into a display voxel value based on a variation between the signal value and a signal value at each corresponding voxel position in a base medical image; and storing, in a storage unit, a color template defining a relationship among a first signal value that is used as a base, a second signal value that is obtained by changing the first signal value, and display voxel values for the first and second signal values, wherein the converting step converts, based on the base medical image, the signal value at each voxel position in the target medical image into the display voxel value with reference to the color template.

19. A non-transitory computer-readable recording medium storing therein a program for causing a computer to execute a medical image conversion method, the program comprising the procedures of:

obtaining a series of a plurality of medical images about a specific region;

converting, with respect to a target medical image to be converted of the series of medical images, a signal value at each voxel position in the target medical image into a display voxel value based on a variation between the signal value and a signal value at each corresponding voxel position in a base medical image; and storing, in a storage unit, a color template defining a relationship among a first signal value that is used as a base, a second signal value that is obtained by changing the first signal value, and display voxel values for the first and second signal values, wherein the converting step converts, based on the base medical image, the signal value at each voxel position in the target medical image into the display voxel value with reference to the color template.

20. A medical image conversion apparatus comprising:
an image obtainment unit that obtains a series of a plurality of medical images about a specific region;
a conversion unit that converts, with respect to a target medical image to be converted of the series of medical images, a signal value at each voxel position in the target medical image into a display voxel value based on a variation between the signal value and a signal value at each corresponding voxel position in a base medical image; and
a storage unit that stores a color template defining a relationship between a first signal value that is used as a base and a display voxel value for the first signal value,
wherein the conversion unit converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the target medical image into the corrected display voxel value.

21. A medical image conversion apparatus comprising:
an image obtainment unit that obtains a series of a plurality of medical images about a specific region;
a conversion unit that converts, with respect to a target medical image to be converted of the series of medical images, a signal value at each voxel position in the target medical image into a display voxel value based on a variation between the signal value and a signal value at each corresponding voxel position in a base medical image; and
a storage unit that stores a color template representing a relationship between a first signal value that is used as a base and a display voxel value for the first signal value,
wherein the conversion unit converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the base medical image into the corrected display voxel value.

22. A medical image conversion method comprising the steps of:
with an image obtainment unit, obtaining a series of a plurality of medical images about a specific region;
with a conversion unit, converting, with respect to a target medical image to be converted of the series of medical images, a signal value at each voxel position in the target medical image into a display voxel value based on a variation between the signal value and a signal value at each corresponding voxel position in a base medical image; and
with a storage unit, storing a color template defining a relationship between a first signal value that is used as a base and a display voxel value for the first signal value,
wherein the converting step converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the target medical image into the corrected display voxel value.

23. A medical image conversion method comprising the steps of:
with an image obtainment unit, obtaining a series of a plurality of medical images about a specific region;
with a conversion unit, converting, with respect to a target medical image to be converted of the series of medical images, a signal value at each voxel position in the target medical image into a display voxel value based on a variation between the signal value and a signal value at each corresponding voxel position in a base medical image; and
with a storage unit, storing a color template representing a relationship between a first signal value that is used as a base and a display voxel value for the first signal value,
wherein the converting step converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the base medical image into the corrected display voxel value.

24. A non-transitory computer-readable recording medium storing therein a program for causing a computer to execute a medical image conversion method, the program comprising the procedures of:
obtaining a series of a plurality of medical images about a specific region;
converting, with respect to a target medical image to be converted of the series of medical images, a signal value at each voxel position in the target medical image into a display voxel value based on a variation between the signal value and a signal value at each corresponding voxel position in a base medical image; and
storing a color template defining a relationship between a first signal value that is used as a base and a display voxel value for the first signal value,
wherein the converting procedure converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the target medical image into the corrected display voxel value.

25. A non-transitory computer-readable recording medium storing therein a program for causing a computer to execute a medical image conversion method, the program comprising the procedures of:

obtaining a series of a plurality of medical images about a specific region;

converting, with respect to a target medical image to be converted of the series of medical images, a signal value at each voxel position in the target medical image into a display voxel value based on a variation between the signal value and a signal value at each corresponding voxel position in a base medical image; and storing a color template representing a relationship between a first signal value that is used as a base and a display voxel value for the first signal value, wherein the converting procedure converts the signal value at each voxel position in the base medical image into the display voxel value with reference to the color template, and corrects the display voxel value corresponding to each voxel position in the base medical image based on an index value representing a variation between the signal value at each voxel position in the target medical image and the signal value at the corresponding voxel position in the base medical image, and converts the signal value at each voxel position in the base medical image into the corrected display voxel value.

* * * * *

UNITED STATES PATENT AND TRADEMARK OFFICE
CERTIFICATE OF CORRECTION

PATENT NO. : 9,295,442 B2
APPLICATION NO. : 13/635605
DATED : March 29, 2016
INVENTOR(S) : Masumoto Page 1 of 1

It is certified that error appears in the above-identified patent and that said Letters Patent is hereby corrected as shown below:

On the title page item [73]

Delete "FUJIFILM Corporation ko, Tokyo (JP)"

Insert --FUJIFILM Corporation, Tokyo (JP)--

Signed and Sealed this
Twenty-eighth Day of June, 2016

Michelle K. Lee
*Director of the United States Patent and Trademark Office*